United States Patent

Kobayashi et al.

[11] 3,996,215
[45] Dec. 7, 1976

[54] STYRYL AND BUTADIENYL SULFO DYE AND PROCESS OF PRODUCING THE DYE

[75] Inventors: Teruo Kobayashi; Masatoshi Sugiyama; Hiroshi Sawaguchi, all of Minami-ashigara, Japan

[73] Assignee: Fuji Photo Film Co., Ltd., Minami-ashigara, Japan

[22] Filed: Sept. 27, 1974

[21] Appl. No.: 510,252

[30] Foreign Application Priority Data

Sept. 27, 1973 Japan .......................... 48-108799

[52] U.S. Cl. .................... 260/240.9; 260/240 D
[51] Int. Cl.² ............ C07D 209/04; C07D 217/00; C07D 263/12
[58] Field of Search ....... 260/240 D, 240.9, 240.65

[56] References Cited
UNITED STATES PATENTS

| | | | |
|---|---|---|---|
| 2,688,540 | 9/1954 | Ganguin et al. | 260/240.9 X |
| 3,257,393 | 6/1966 | Vinton | 260/240.9 |
| 3,379,723 | 4/1968 | Clarke | 260/240.9 |
| 3,544,325 | 12/1970 | Depoorter et al. | 260/240.9 UX |
| 3,652,283 | 3/1972 | Mackey | 260/240.9 UX |
| 3,687,670 | 8/1972 | Rillaers et al. | 260/240.9 X |
| 3,855,209 | 12/1974 | Hoyle, Jr. | 260/240.9 X |

FOREIGN PATENTS OR APPLICATIONS

| | | | |
|---|---|---|---|
| 1,547,824 | 11/1969 | Germany | 260/240.65 |
| 2,202,300 | 8/1973 | Germany | 260/240.9 |

*Primary Examiner*—Allen B. Curtis
*Attorney, Agent, or Firm*—Sughrue, Rothwell, Mion, Zinn & Macpeak

[57] ABSTRACT

A styryl and butadienyl dye suitable as a filter dye or antihalation dye for photography having the formula

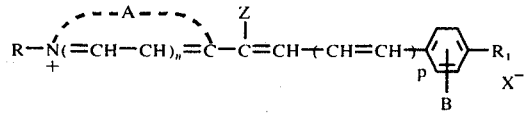

wherein R represents a lower alkyl group, an unsubstituted or substituted sulfo lower alkyl group, an unsubstituted or substituted sulfo lower alkenyl group, or a carboxy lower alkyl group; A represents an atom necessary for forming a 5-membered or 6-membered heterocyclic ring; Z represents a hydrogen atom, a methyl group, or a phenyl group; B represents a hydrogen atom, a lower alkyl group, a hydroxyl group, an alkoxy group, a halogen atom, a nitro group, a carboxyl group, an unsubstituted or substituted acylamino group, an alkoxycarbonylamino group, an alkylsulfonylamino group, or an alkylthio group; $R_1$ represents $-OR_2$ or

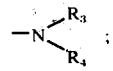

$R_2$ represents an unsubstituted or substituted sulfo lower alkyl group; $R_3$ and $R_4$, which may be the same or different, each represents a hydrogen atom, an unsubstituted or substituted alkyl group, an unsubstituted or substituted aralkyl group, an unsubstituted or substituted aryl group, an arylsulfonyl group, or an acetyl group; at least one of $R_3$ and $R_4$ containing at least one sulfo group; $X^-$ represents an acid anion; and $n$ and $p$ each represents 0 or 1.

17 Claims, No Drawings

STYRYL AND BUTADIENYL SULFO DYE AND PROCESS OF PRODUCING THE DYE

BACKGROUND OF THE INVENTION

1. Field of the Invention

The present invention relates to styryl and butadienyl dyes and, more particularly, the invention relates to water-soluble styryl and butadienyl dyes suitably used as filter dyes or antihalation dyes for photographic materials. The invention further relates to a process of producing these styryl and butadienyl dyes.

2. Description of the Prior Art

Water-soluble styryl and butadienyl dyes for use as photographic dyes are described in, for example, the specifications of U.S. Pat. Nos. 3,384,487 and 3,423,207. These known dyes have a sulfo group on the heterocyclic ring containing a quaternary ammonium atom but these known dyes are still insufficient in properties required in photography, such as, solubility, decolorizability, and photographic property.

SUMMARY OF THE INVENTION

An object of this invention is, therefore, to provide water-soluble styryl and butadienyl dyes having high solubility and decolorizability.

Another object of this invention is to provide water-soluble styryl and butadienyl dyes which can be suitably used as filter dyes or antihalation dyes in photography.

Still another object of this invention is to provide a process for producing water-soluble styryl and butadienyl dyes having improved properties.

It has now been found that the aforementioned properties of a styryl and butadiene dye having a heterocyclic ring containing a quaternary ammonium salt at one end of the methylene chain thereof and a phenyl group at the other end of the methylene chain are improved by introducing a sulfo group as a substituent on the phenyl group not directly but through a carbon bond.

That is, according to the present invention, there is provded a styryl and butadiene dye represented by formula (I)

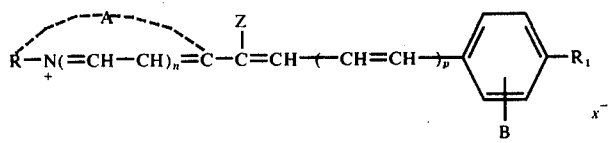

wherein R represents a lower alkyl group, an unsubstituted or substituted sulfo lower alkyl group, an unsubstituted or substituted sulfo lower alkenyl group, or a carboxy lower alkyl group; A represents the atoms necessary for forming a 5-membered or 6-membered heterocyclic ring; Z represents a hydrogen atom, a methyl group, or a phenyl group; B represents a hydrogen atom, a lower alkyl group, a hydroxyl group, an alkoxy group, a halogen atom, a nitro group, a carboxyl group, an unsubstituted or substituted acylamino group, an alkoxycarbonylamino group, an alkylsulfonylamino group, or an alkylthio group; $R_1$ represents $-OR_2$ or

$R_2$ represents an unsubstituted or substituted sulfo lower alkyl group; $R_3$ and $R_4$, which may be the same or different, each represents a hydrogen atom, an unsubstituted or substituted alkyl group, an unsubstituted or substituted aralkyl group, an unsubstituted or substituted aryl group, an arylsulfonyl group, or an acetyl group with at least one of $R_3$ and $R_4$ containing, however, at least one sulfo group; $X^-$ represents an acid anion; and $n$ and $p$ each represents 0 or 1.

The styryl and butadienyl dye represented by general formula (I) can be produced by condensing an aldehyde compound having a sulfo group represented by formula (II)

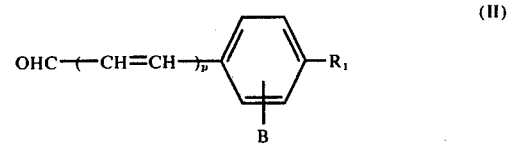

and a cyclic quaternary ammonium salt represented by the formula (III)

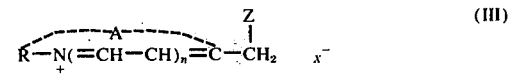

wherein in the above formulae, R, $R_1$, A, B, X, Z, $n$ and $p$ have the same significance as in general formula (I).

DETAILED DESCRIPTION OF THE INVENTION

The styryl and butadienyl dye of this invention is represented by general formula (I) as indicated above.

In the general formula R represents a lower alkyl group (e.g., having 1 to 6 carbon atoms) such as a methyl group, an ethyl group, a propyl group, and a butyl group; an unsubstituted or substituted sulfo lower alkyl group (e.g., having 1 to 6 carbon atoms in the alkyl moiety thereof, and having as substituents a methyl group, an ethyl group, a phenyl group, a hydroxy group, a fluorine atom, etc.) or sulfo lower alkenyl group (e.g., having 2 to 6 carbon atoms in the alkenyl moiety thereof, and having as substituents a methyl group, an ethyl group, a phenyl group, a hydroxy group, a fluorine atom, etc.), such as, a sulfoethyl group, a 3-sulfopropyl group, a 3-sulfobutyl group, a 4-sulfobutyl group, a 5-sulfopentyl group, a 1-methyl-3-sulfopropyl group, a 2-hydroxy-3-sulfopropyl group, a 2,4-diphenyl-4-sulfobutyl group, a 4-ethyl-4-sulfobutyl group, a 3-sulfopropenyl group, and a 1,1,1,2-tetrafluoro-2-sulfoethyl group; or a carboxy lower alkyl group (e.g., having 1 to 6 carbon atoms in the alkyl moiety thereof) such as a 2-carboxyethyl group, a 3-carboxypropyl group, and a 4-carboxybutyl group.

A represents the atoms necessary for forming a 5- or 6-membered heterocyclic ring and examples of such heterocyclic rings are, for example, thiazole (e.g., thiazole, 4-methylthiazole, 4-phenylthiazole, 5-methylthiazole, 5-phenylthiazole, 4,5-dimethylthiazole, 4,5-diphenylthiazole, 4-(2-thienyl)thiazole, etc.), benzothiazole (e.g., benzothiazole, 4-chlorobenzothiazole, 5-chlorobenzothiazole, 6-chlorobenzothiazole, 7-chlorobenzothiazole, 4-methylbenzothiazole, 5-methylbenzothiazole, 6-methylbenzothiazole, 5-bromobenzothiazole, 6-bromobenzothiazole, 5-phenylbenzothiazole, 5-phenylbenzothiazole, 4-methoxybenzothiazole, 5-methoxybenzothiazole, 6-methoxybenzothiazole, 5iodobenzothiazole, 6-iodobenzothiazole, 4-ethoxybenzothiazole, 5-ethoxybenzothiazole, tetrahydrobenzothiazole, 5,6-dimethoxybenzothiazole, 5,6-dioxymethylenebenzothiazole, 5-hydroxybenzothiazole, 6-hydroxybenzothiazole, 5-(3'-sulfopropyloxy)benzothiazole, 6-sulfobenzothiazole, 5-methyl-6-sulfobenzothiazole, etc.), naphthothiazole (e.g., naphtho[2,1-d]thiazole, naphtho[1,2-d]thiazole, 5-methoxynaphtho[2,3-d]thiazole, 5-ethoxynaphtho[2,3-d]thiazole, 8-methoxynaphtho[2,3-d]thiazole, 7-methoxynaphtho[2,3-d]thiazole, 4'-methoxythianaphtheno-7',6'-4,5-thiazole, etc.), oxazole (e.g., 4-methyloxazole, 5-methyloxazole, 4-phenyloxazole, 4,5-diphenyloxazole, 4-ethyloxazole, 4,5-dimethyloxazole, 5-phenyloxazole, etc.), benzoxazole (e.g., benzoxazole, 5-chlorobenzoxazole, 5-methylbenzoxazole, 5-phenylbenzoxazole, 6-methylbenzoxazole, 5,6-dimethylbenzoxazole, 4,6-dimethylbenzoxazole, 5-methoxybenzoxazole, 5-ethoxybenzoxazole, 5-chlorobenzoxazole, 6-methoxybenzoxazole, 5-hydroxybenzoxazole, 6-hydroxybenzoxazole, 5-sulfobenzoxazole, etc.), naphthoxazole (e.g., naphtho[2,1-d]oxazole, naphtho[1,2-d]oxazole, etc.), indole (e.g., 3,3-dimethylindole, 5-chloro-3,3-dimethylindole, 3,3-dimethyl-5methoxyindole, 3-ethyl-3-methyl-5-nitroindole, 3,3-dimethyl-5-ethoxycarbonylindole, 3,3-dimethyl-5-propylindole, 3-(2'-dimethylaminoethyl)-3-methyl-5-methoxyindole, 3,5-dimethyl-3-(2'-phenoxyethyl)indole, etc.), benzindole (e.g., 3,3-dimethylbenz[e]indole monosulfonate, etc.), selenazole, benzselenazole and naphthoselenazole (e.g., 4-methylselenazole, 4-phenylselenazole, benzoselenazole, 5-chlorobenzoselenazole, 5-methoxybenzoselenazole, 5-hydroxybenzoselenazole, tetrahydrobenzoselenazole, naphtho[2,1-d]selenazole, naphtho[1,2-d]selenazole, etc.), pyridine (e.g., pyridine, 4-phenylpyridine, 4,6-diphenylpyridine, 6-chloro-5-nitropyridine, 3-sulfopyridine, etc.), quinoline and isoquinoline (e.g., 2-quinoline, 3-methyl-2-quinoline, 5-ethyl-2-quinoline, -6-chloro-2-quinoline, 8-chloro-2-quinoline, 6-methoxy-2-quinoline, 8-ethoxy-2-quinoline, 8-hydroxy-2-quinoline, 4-quinoline, 6-methoxy-4-quinoline, 7-methyl-4-quinoline, 8-chloro-4-quinoline, 1-isoquinoline, 3,4-dihydro-1-isoquinoline, 3-isoquinoline, etc.), and benzimidazole (e.g., benzimidazole, 5-methylbenzimidazole, 5-chlorobenzimidazole, 6-methylbenzimidazole, etc.) rings. These heterocyclic rings can be unsubstituted or substituted. Examples of suitable substituents on the heterocyclic ring are one or more of an alkyl group having 1 to 4 carbon atoms (such as a methyl group, an ethyl group, a propyl group, etc.), a carboxy group, an ethoxycarbonyl group, a methoxy group, an ethoxy group, an acetyloxy group, a halogen atom (such as chlorine, bromine, etc.), a phenyl group, a 4'-sulfophenyl group, a hydroxy group, a 3'-sulfopropyloxy group, a sulfo group and a nitro group.

Z represents a hydrogen atom, a methyl group, or a phenyl group.

B represents a hydrogen atom; a lower alkyl group (e.g., having 1 to 4 carbon atoms) such as a methyl group and an ethyl group; a hydroxyl group; an alkoxy group (e.g., having 1 to 4 carbon atoms in the alkyl moiety thereof) such as a methoxy group, an ethoxy group, a propoxy group, and a butoxy group; a halogen atom; a nitro group; a carboxyl group; an unsubstituted or substituted acylamino group such as an acetylamino group, a benzoylamino group, a chloroacetylamino group, and a hydroxyacetylamino group; an alkoxycarbonylamino group such as a methoxycarbonylamino group, an ethoxycarbonylamino group, a propoxyamino group, etc.; an alkylsulfonylamino group (e.g., having 1 to 4 carbon atoms in the alkyl moiety thereof) such as a methylsulfonylamino group, an ethylsulfonylamino group, a propylsulfonylamino group, etc.; or an alkylthio group (e.g., having 1 to 4 carbon atoms in the alkyl moiety thereof). $R_1$ represents —$OR_2$ or

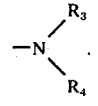

$R_2$ represents an unsubstituted or substituted sulfo lower alkyl group (e.g., having 1 to 6 carbon atoms in the alkyl moiety thereof) such as a sulfoethyl group, a 3-sulfopropyl group, a 5-sulfopentyl group, a 1-methyl-3-sulfopropyl group, and a 2-hydroxy-3-sulfopropyl group and $R_3$ and $R_4$, which may be the same or different, each represents a hydrogen atom; an alkyl group (e.g., having 1 to 18 carbon atoms, such as a methyl group, an ethyl group, a butyl group, a cyclohexyl group, and a dodecyl group); a substituted alkyl group (e.g., having 1 to 6 carbon atoms in the alkyl moiety thereof, for example, a cyanoalkyl group such as a 2-cyanoethyl group, a 3-cyanopropyl group, etc., a sulfoalkyl group such as a 2-sulfoethyl group, a 3-sulfopropyl group, a 4-sulfobutyl group, a 5-sulfopentyl group, a 1-methyl-3-sulfopropyl group, a 2-hydroxy-3-sulfopropyl group, etc., a hydroxyalkyl group such as a 2-hydroxyethyl group, a 3-hydroxypropyl group, etc., a dihydroxyalkyl group such as a 2,3-dihydroxypropyl group, etc., a haloalkyl group such as a 2-chloroethyl group, a 3-chloro-2-hydroxypropyl group, etc., a carboxyalkyl group such as a 2-carboxyethyl group, a 2-carboxypropyl group, a 3-carboxypropyl group, etc., an alkoxycarbonylalkyl group (e.g., having 1 to 4 carbon atoms in the alkoxy moiety thereof) such as a methoxycarbonylethyl group, an ethoxycarbonylethyl group, etc., an acylalkyl group (e.g., having 1 to 4 carbon atoms in the acyl moiety thereof) such as an acetylethyl group, etc., an acyloxyalkyl group (e.g., having 1 to 6 carbon atoms in the acyl moiety thereof) such as an acetyloxyethyl group, a benzoyloxyethyl group, etc., an alkoxyalkyl group (e.g., having 1 to 4 carbon atoms in the alkoxy moiety thereof) such as a methoxyethyl group, an ethoxypropyl group, etc., an aryloxyalkyl group such as a phenoxyethyl group, etc., a cyanoalkoxyalkyl group (e.g., having 1 to 4 carbon atoms in the alkoxy moiety thereof) such as a cyanoethoxyethyl group, etc., a dialkylaminoalkyl group (e.g., having 1 to 4 carbon atoms in the alkyl moiety on the amino moiety) such as an N,N-dimethylaminomethyl group, etc., an alkylarylaminoalkyl group (e.g., having 1 to 4 carbon atoms in the alkyl moiety on the aryl moiety) such as an N-methyl-N-phenylaminoethyl group, etc., an acylaminoalkyl group (e.g., having 1 to 4 carbon atoms in the acyl moiety thereof) such as an acetylaminopropyl group, etc., an alkylsulfonylaminoalkyl group (e.g., having 1 to 4 carbon atoms in the alkyl moiety on the sulfonyl moiety) such as a methylsulfonylaminoethyl group, etc., an acylacyloxyalkyl group such as an acetylacetoxyethyl group, etc., an aryloxyacyloxyalkyl group such as a phenoxyacetoxyethyl group, etc., an alkylsulfonylalkyl group (e.g., having 1 to 4 carbon atoms in the alkyl moiety on the sulfonyl moiety) such as an ethylsulfonylethyl group, etc., an alkylsulfonyloxyalkyl group (e.g., having 1 to 4 carbon atoms in the alkyl moiety on the sulfonyl moiety) such as a methylsulfonyloxyethyl group, etc., an alkylthioalkyl group (e.g., having 1 to 4 carbon atoms in the alkyl moiety on the thio moiety) such as an ethylthioethyl group, etc., and an alkoxycarbonyloxyalkyl group (e.g., having 1 to 4 carbon atoms in the alkoxy moiety thereof) such as an ethoxycarbonyloxyethyl group, etc.); an aralkyl group (e.g., having 1 to 2 carbon atoms in the alkyl moiety thereof, such as a benzyl group and a phenylethyl group); a substituted aralkyl group (e.g., having 1 to 2 carbon atoms in the alkyl moiety thereof, and containing one or more substituents such as a sulfo group, an alkyl group having 1 to 3 carbon atoms such as a methyl group, an ethyl group, etc., an alkoxy group having 1 to 3 carbon atoms such as a methoxy group, an ethoxy group, etc., e.g., a p-methoxybenzyl group, a p-sulfobenzyl group, a p-sulfophenylethyl group, and a p-methylphenylethyl group); an aryl group such as a phenyl group; a substituted aryl group (e.g., containing one or more substituents such as a sulfo group, an alkyl group having 1 to 3 carbon atoms, e.g., a methyl group, an ethyl group, etc., an alkoxy group having 1 to 3 carbon atoms, e.g., a methoxy group, an ethoxy group, a halogen atom, e.g., a chlorine atom, a bromine atom, etc., such as a p-methylphenyl group, a p-sulfophenyl group, and a 4-methyl-3-sulfophenyl group); an arylsulfonyl group; or an acetyl group. At least one of the $R_3$ and $R_4$ groups contains at least one sulfo group.

$X^-$ represents an acid anion such as a halogen ion, an alkyl sulfate ion (e.g., having 1 to 4 carbon atoms in the alkyl moiety thereof) such as a methyl sulfate ion, an alkylaryl sulfonate ion (e.g., having 1 to 4 carbon atoms in the alkyl moiety thereof) such as a p-toluene sulfonate ion, and a thiocyanate ion. $n$ is 0 and 1 and $p$ is 0 or 1.

The sulfo group of the dye of this invention can form a salt such as an alkali metal salt (e.g., a sodium salt, potassium salt, etc.), an alkaline earth metal salt (e.g., a calcium salt, etc.); an ammonium salt, or an amine salt (e.g., a triethylamine salt, a pyridine salt, etc.) or can form an intramolecular salt.

As described above, the styryl and butadienyl dye of this invention represented by formula (I) can be produced by the condensation of a sulfo group-containing aldehyde compound represented by general formula (II) and a cyclic quaternary ammonium salt of general formula (III) according to the process of this invention.

It is advantageous to conduct the condensation reaction in a solvent having the ability to dissolve the starting materials. Examples of suitable solvent which can be used are alcohols such as methanol, ethanol, isopropanol, etc.; ethyleneglycol monoalkyl ethers such as ethyleneglycol monomethyl ether, etc.; amides such as acetamide, dimethylformamide, etc.; dimethylsulfoxide; chloroform; and carboxylic acids such as fumaric acid, oxalic acid, acetic acid, etc. These solvents can be used individually or as a mixture thereof. And a suitable amount of the solvent used can range from about 0.1 to 50 times by weight, preferably 2 to 20 times by weight the amount of the starting materials. The condensation reaction can be generally carried out at a temperature range of from about 0° C to the boiling point of the solvent used. It is preferable for promoting the reaction to add pyridine, piperidine, diethylamine, triethylamine, ammonia, potassium acetate, etc., to the reaction system. A suitable amount of the promotor can range from about 0 to 50 times by weight, preferably 0 to 1 times by weight the weight of the starting materials. The period of time for reaction is usually from about 10 minutes to 24 hours. It is preferred that the ratio of the aldehyde compound of formula (II) and the cyclic quaternary ammonium salt of formula (III) be an equi-molar ratio but, if desired, one of the reactants can be present in excess, for example, in an amount of up to about 2:1 to 1:2 on a molar basis.

The aldehyde compound represented by formula (II) can be prepared using known methods. For example, the aldehyde compound of formula (II) wherein $p$ is 0 can be prepared according to the Vilsmeier and Hack reaction described in *Berichte*, Vol. 60, 119 (1927) in which dimethylformamide is used as the formylating agent and further phosphorus oxychloride is used or according to the method described in the specification of British Pat. No. 794,885 in which hexamethylenetetramine and formaldehyde are reacted using a lower fatty acid such as acetic acid and/or the anhydride thereof or a polycarboxylic acid as the reaction solvent in the presence of a mineral acid as the case may be.

The aldehyde compound as described above can further be prepared by the method described in *Berichte*, Vol. 96, 308 (1963) in which a dichloromethyl alkyl ether is formylated using a Friedel-Crafts catalyst such as aluminum chloride and zinc chloride. The aldehyde compound can also be prepared by the so-called Duff reaction described in *Journal of the Chemical Society*, 276 (1945) in which hexamethylenetetramine is heated in an alcohol with the addition of a mixture of acetic acid and formic acid. Furthermore, the aldehyde compound can be prepared by the so-called Gattermann-Koch reaction described in *Berichte*, Vol. 30, 1622 (1897) in which formylation is carried out using anhydrous aluminum chloride together with carbon monoxide and hydrochloric acid. Gattermann further reported the method wherein anhydrous HCN is used in place of carbon monoxide as described in *Annalen*, Vol. 347, 347 (1906). Moreover, the so-called Reimer-Tiemann reaction as described in *Berichte*, Vol. 9, 824 (1876) can be also employed in which the formylation is conducted using chloroform and an alkali.

Other examples of methods of producing the above-described aldehyde compound are the condensation of formaldehyde as described in the specifications of German Pat. Nos. 105,103 and 105,798, the condensation of chloral as described in the specification of French Pat. No. 791,818, the condensation of alloxane, oxalyl ester acid chloride, and sodium glyoxalate as described in the specifications of German Pat. Nos. 107,720 and 115,817, and the condensation of chloromethylene dibenzoate as described in *Berichte*, Vol. 41, 1035

(1908). These methods as described above are all reactions involving the direct introduction of an aldehyde group. Furthermore, other formylation methods include following indirect methods.

That is, the chemical oxidation as described in the specification of U.S. Pat. No. 1,302,273; *Journal of the Chemical Society*, Vol. 91, 258 (1907); the specification of German Pat. No. 121,785; *Journal of the Chemical Society*, 2310 (1932); and Annalen, Vol. 311, 363 (1900); the oxidation of substituted benzyl alcohol as described in *Journal of the Chemical Society*, Vol. 71, 1051 (1897) and *Journal of Organic Chemistry*, Vol. 6, 437 (1941); the oxidation of benzyl halide as described in *Journal of the American Chemical Society*, Vol. 56, 2056 (1934); the oxidation of acetophenone; the oxidation of naphthalene; the reduction of an acid; and the reduction of an ester; can also be employed for producing the aldehyde compounds used in this invention.

The aldehyde compound of formula (II) wherein $p$ is 1 can be produced by the method similar to the Vilsmeier reaction as described in *Berichte*, Vol. 91, 850 (1958) using N-methylanilinopropane(1)-al(3) and an appropriate unsubstituted or substituted aniline or phenol. Also, the aldehyde compound can be obtained by the reaction of the corresponding unsubstituted or substituted aminobenzaldehyde and paraldehyde as described in *Berichte*, Vol. 61, 2074 (1928). Also, the aldehyde compound can be prepared by the method described in Japanese Patent Publication No. 3183/1968 in which an irenal (that is, a phosphorane compound having a phosphorus-irene atomic group and an aldehyde group conjugated therewith) is reacted with a substituted benzaldehyde. The substituted aniline or phenol used above can be prepared using well known methods which are well known in organic chemistry.

Typical examples of aldehyde compounds represented by general formula (II) are illustrated below:

II-1
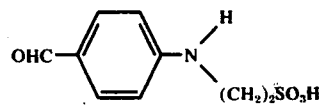

II-2
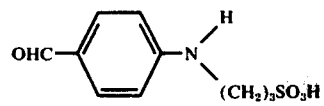

II-3
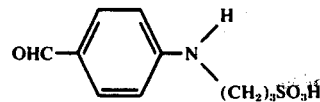

II-4
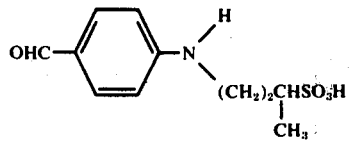

II-5
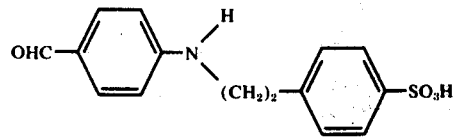

II-6
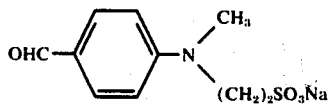

II-7
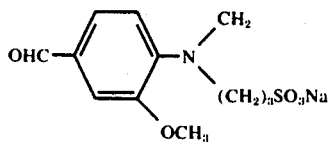

-continued
II-8
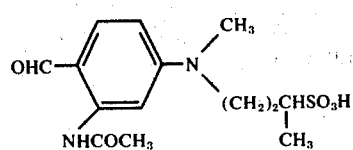
II-9
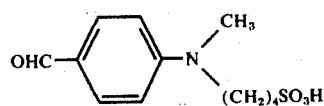
II-10
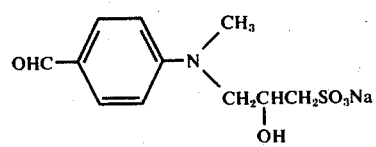
II-11
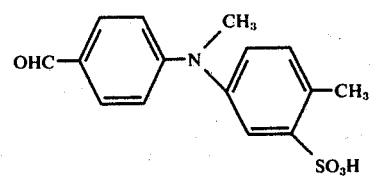
II-12
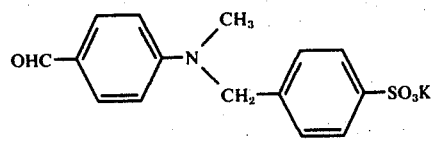
II-13
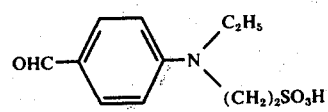
II-14
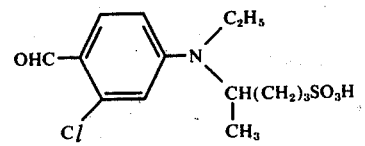
II-15
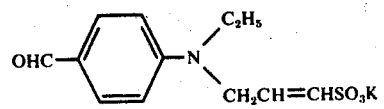
II-16
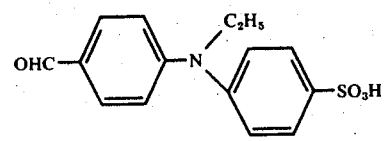

II-17 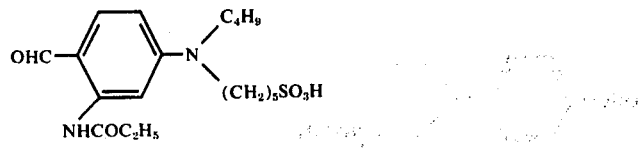
II-18 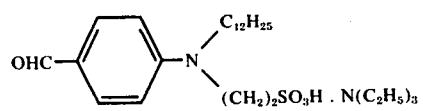
II-19 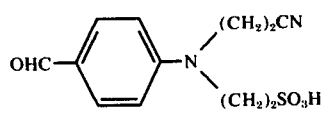
II-20 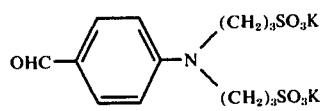
II-21 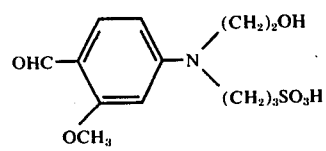
II-22 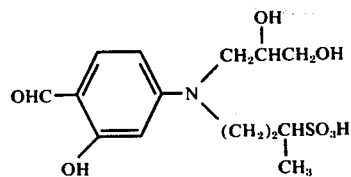
II-23 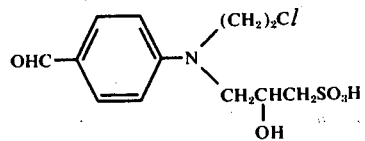
II-24 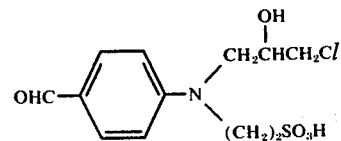
II-25 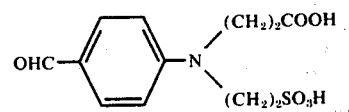

II-26 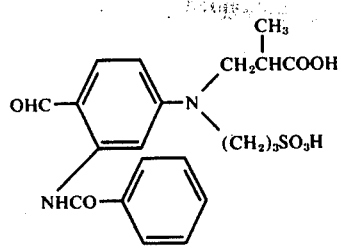
II-27 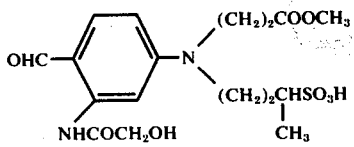
II-28 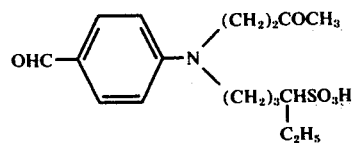
II-29 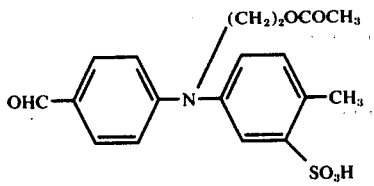
II-30 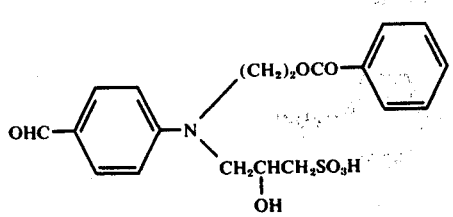
II-31 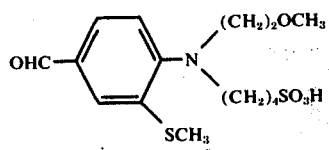
II-32 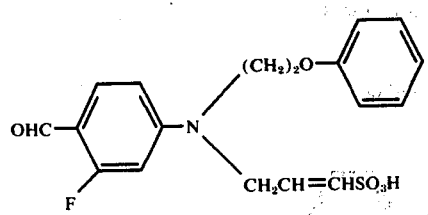
II-33 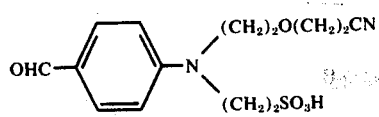

-continued
II-34
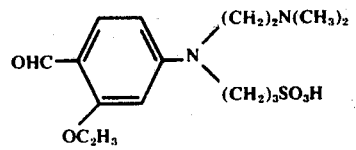
II-35
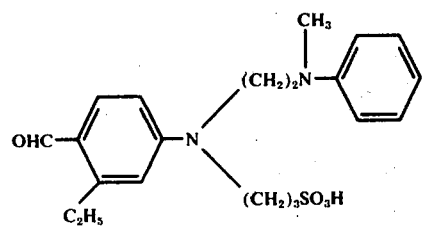
II-36
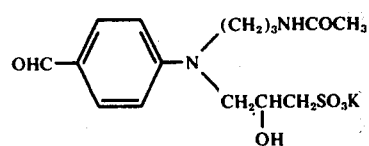
II-37
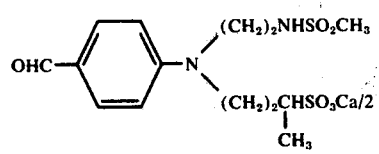
II-38
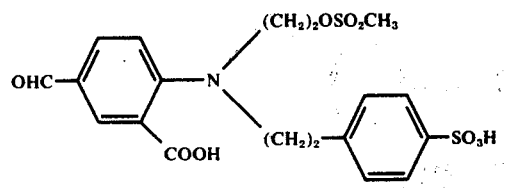
II-39
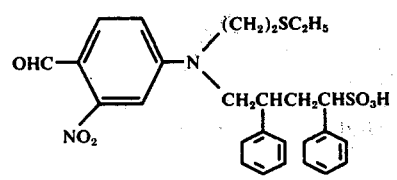
II-40
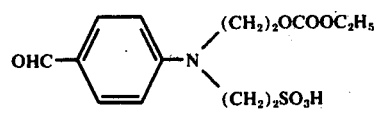
II-41
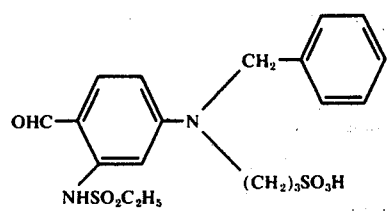

II-42
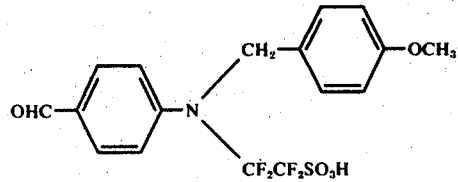
II-43
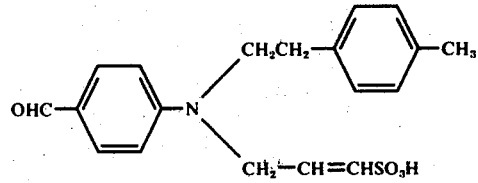
II-44
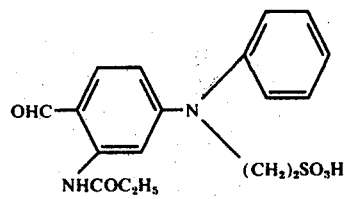
II-45
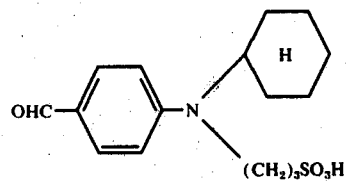
II-46
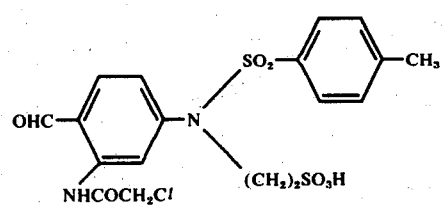
II-47
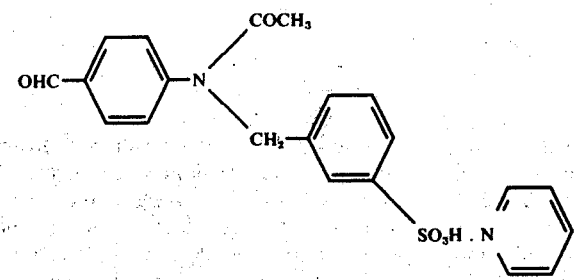
II-48
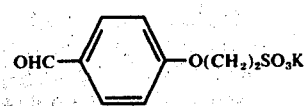

II-49
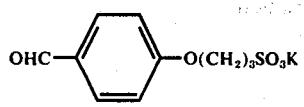

II-50
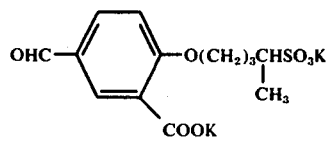

II-51
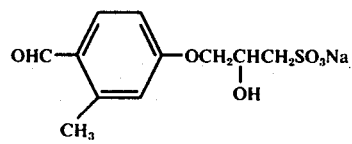

II-52
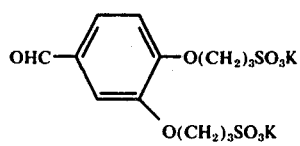

II-53
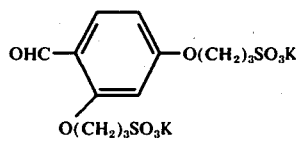

II-54
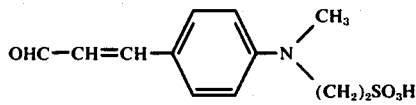

II-55
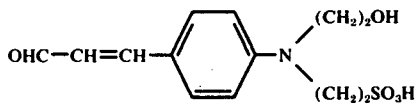

II-56
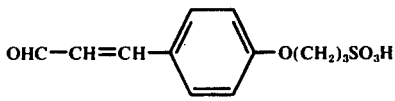

Then, the cyclic quaternary ammonium salts represented by formula (III) can be also prepared by known methods, e.g., as disclosed in Berichte, Vol. 30, 2254 (1897), Berichte, Vol. 84, 96 (1951), Journal of the Chemical Society, 2685 (1930), etc., for oxazole and benzoxazole materials, in Berichte, Vol. 31, 1496 (1898), Berichte, Vol. 19, 1563 (1886), etc., for indole materials, and in Annalen, Vol. 250, 265 (1889), German Pat. No. 670,131, etc., for thiazole materials. That is, the cyclic quaternary ammonium salt having a sulfo group can be prepared by directly sulfonating a corresponding base with various complexes (such as a pyridine complex and dioxane complex) of sulfuric acid, fuming sulfuric acid, or sulfuric anhydride or the cyclic quaternary ammonium salt can also be prepared by forming a sulfonate using a suitable sulfonated amine such as sulfonated 2-aminophenol and sulfuric anhydride and then treating the sulfonate with a quaternary chlorinating agent having the formula RX, wherein R and X have the same significance as in general formula (I).

Typical examples of quaternary chlorinating agents of the formula RX are an alkyl halide such as methyl iodide, butyl iodide, 1-sulfoethyl-2-iodide, and the corresponding alkyl bromides; a dialkyl sulfate such as dimethyl sulfate, and diethyl sulfate; an alkylaryl sulfonate such as methyl p-toluenesulfonate, butyl p-toluenesulfonate, etc.; an alkanesultone having at least 3 carbon atoms such as 3-propanesultone, 1,4-butanesultone, 2,4-butanesultone, and isohexyl sultone; and a lactone such as propiolactone, γ-butyrolactone, γ-valerolactone, and 2-valerolactone.

Furthermore, the cyclic quaternary ammonium salt of formula (III) which does not have a sulfo group at the heterocyclic ring can be obtained by quaternarizing an appropriate corresponding base with the aforesaid quaternary chlorinating agent.

The aforesaid reaction can be conducted by methods well known in organic chemistry.

Typical examples of cyclic quaternary ammonium salts represented by formula (III) are illustrated below:

III-1

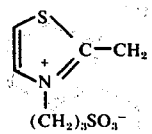

III-2

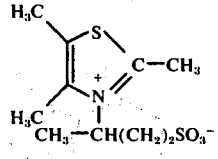

III-3

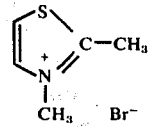

III-4

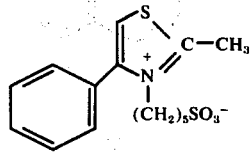

III-5

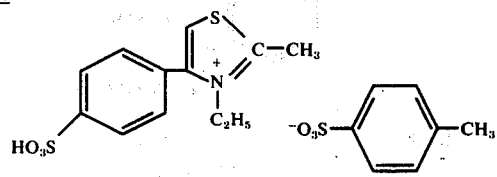

III-6

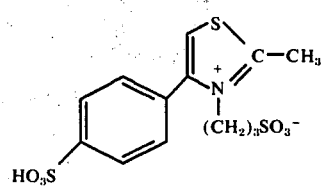

III-7

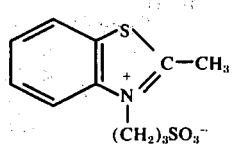

III-8

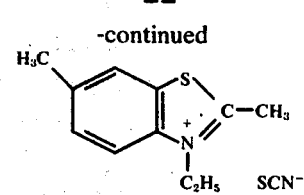

III-9

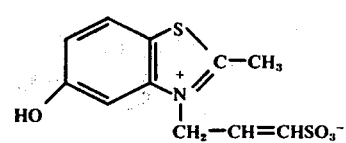

III-10

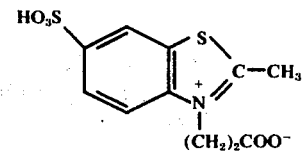

III-11

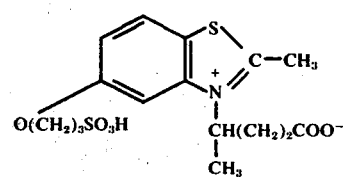

III-12

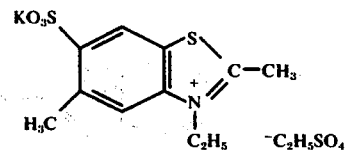

III-13

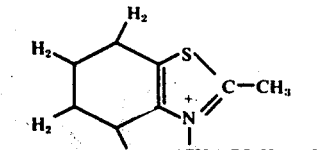

III-14

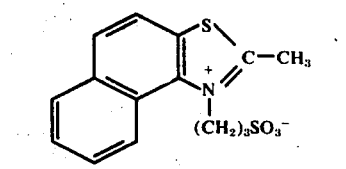

III-15

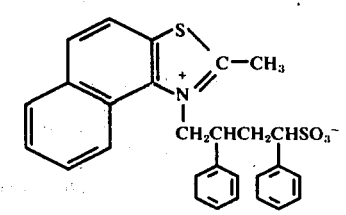

III-16

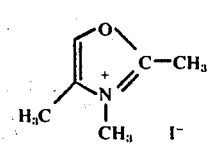

-continued
III-17 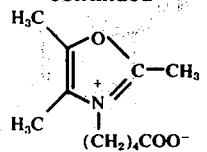
III-18 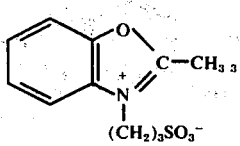
III-19 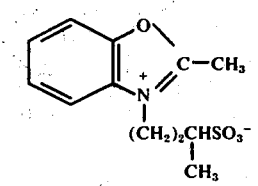
III-20 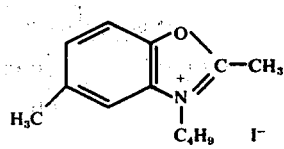
III-21 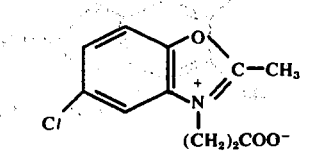
III-22 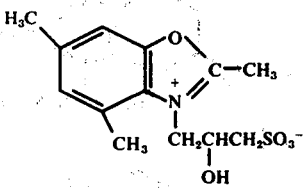
III-23 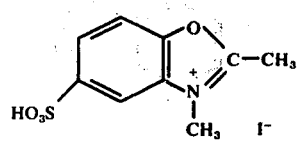
III-24 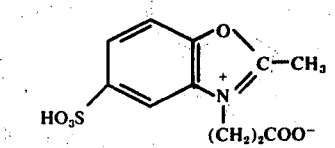
III-25 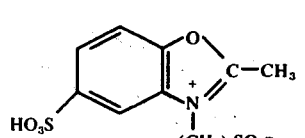
-continued
III-26 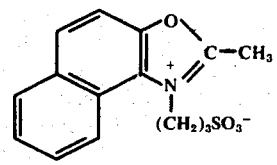
III-27 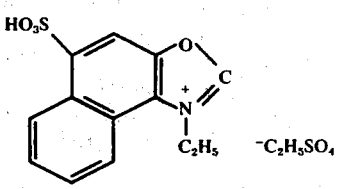
III-28 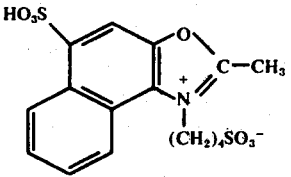
III-29 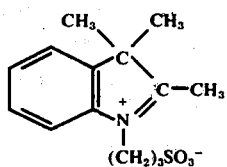
III-30 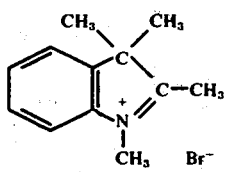
III-31 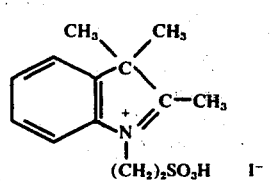
III-32 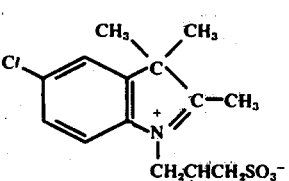
III-33 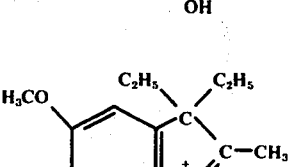

III-34 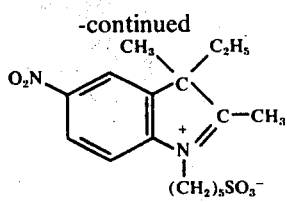
III-35 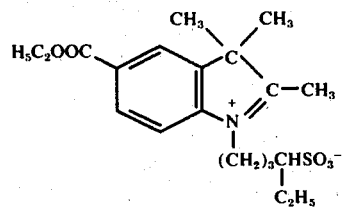
III-36 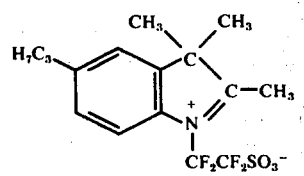
III-37 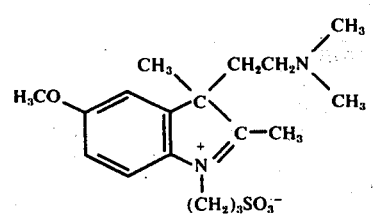
III-38 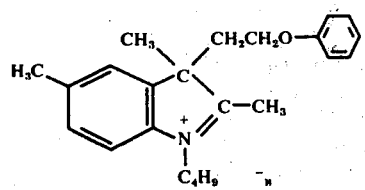
III-39 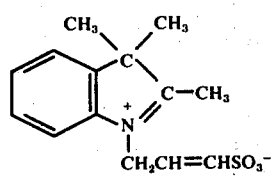
III-40 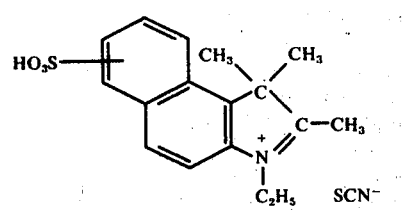
III-41 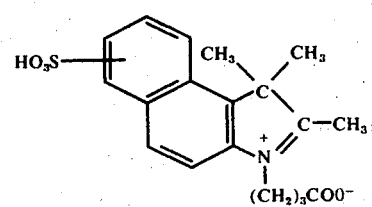
III-42 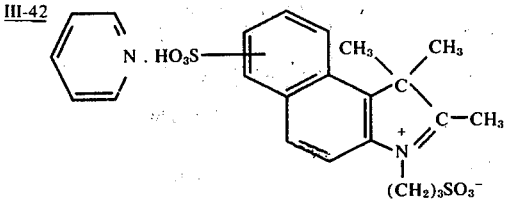
III-43 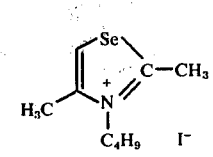
III-44 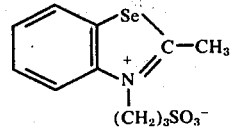
III-45 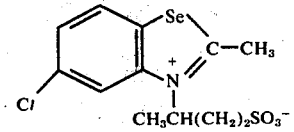
III-46 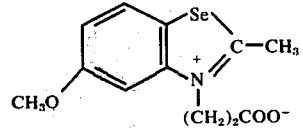
III-47 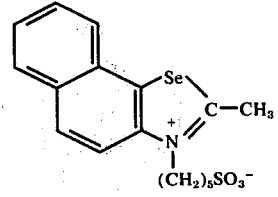
III-48 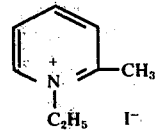
III-49 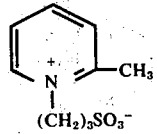
III-50 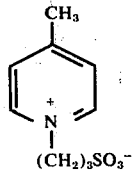

III-51 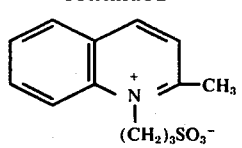

III-52 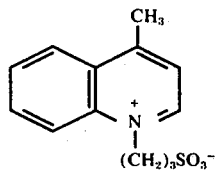

III-53 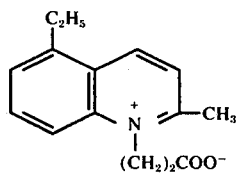

III-54 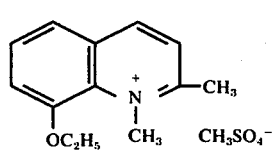

III-55 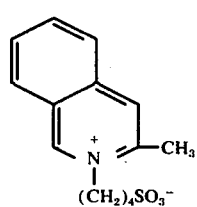

III-56 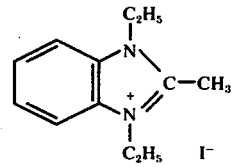

III-57 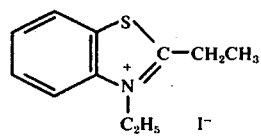

III-58 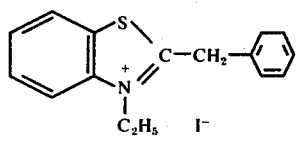

III-59 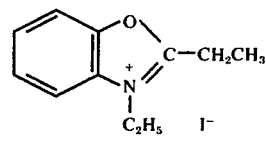

III-60 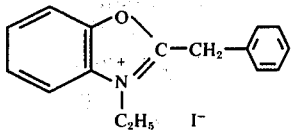

A feature of the styryl and butadienyl dye of this invention represented by formula (I) is that the group represented by $R_1$ contains a sulfo group and as a result of this feature the dye of this invention is clearly distinguished from known styryl and butadienyl dyes. Also, it has been confirmed that the styryl and butadienyl dye of this invention having a sulfo group on the $R_1$ group shows excellent decolorizability by sodium sulfite as compared with conventional dyes having a sulfo group at a cyclic quaternary ammonium salt portion (corresponding to group R of formula (I)). Furthermore, the dye of this invention can have sulfo groups on the moieties of both sides of the methine chain, whereby the property of the dye can be greatly improved as compared with conventional dyes. That is, the styryl and butadienyl dye of this invention can contain a higher proportion of sulfo group per molecule than conventional styryl and butadienyl dyes, whereby the dye of this invention has improved solubility in water. Therefore, the dye of this invention is also excellent in decolorizability by dissolving out besides the high decolorizability by sulfite ions and thus can be decolored complete-irreversibly by photographic processing. Still further, by introducing an acid group into the dye of this invention, a solution or a colored film or layer of the dye with improved stability can be obtained without adversely influencing the photographic property thereof. Moreover, the dye of this invention in which a sulfoalkyl group or a sulfobenzyl group has been introduced into the phenyl nucleus of the aldehyde compound through a nitrogen atom or an oxygen atom does not exhibit the disadvantage in which the color density (absorbance) tends to be reduced as is the situation with the conventional dye having a sulfo group directly at the phenyl nucleus of the aldehyde compound. This is because the electronic effect of the sulfo group is intercepted by the alkyl group and thus resonance of the dye molecule does not occur. Also, since the dye of this invention can have sulfo groups at the nuclei bonded to both sides of the methine chain as described above, if the nuclei are cleaved at the methine chain by hydrolysis or for other reasons, the nuclei are dissolved in water and hence the dye of this invention can be said to be a quite excellent dye from the standpoint of pollution prevention.

The styryl and butadienyl dye of this invention having the above described excellent properties is particularly suitable as a filter dye, an antihalation dye, an anti-irradiation dye, etc., for photographic materials. Also, the dye of this invention, a sulfoalkyl group being introduced thereto, has good solubility in methanol and thus can be effectively used as a coloring dye for a resin back.

The invention will be explained in greater detail by reference to the following examples. Unless otherwise indicated, all parts, percents, ratios and the like are by weight.

EXAMPLE 1

Preparation of the dye having the following formula:

Dye No. I-1

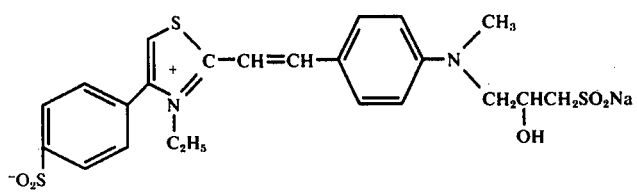

A mixture of 2.8 g of Aldehyde Compound II-10, 4-N-methyl-N-(2-hydroxy-3-sulfopropyl)aminobenzaldehyde sodium salt, 5.2 g of Cyclic Quaternary Ammonium Salt III-5, 3-ethyl-2-methyl-4-p-sulfophenyl-thiazolium.p-toluenesulfonate, 0.5 ml of piperidine and 60 ml of ethanol was refluxed for 1.5 hours. The reaction mixture was, then, cooled, the dye thus precipitated was recovered by filtration and immersed overnight in acetone. The dye was then collected by filtration, dried and recrystallized from methanol to provide 3.2 g of the dye. An aqueous solution of the dye had an orange color and the absorption maximum wavelength of the dye was 492 m$\mu$. $E_{max} = 3.3 \times 10^4$. The color of a gelatin film dyed with the dye is shown in the following table.

Various dyes having a thiazole nucleus were also prepared in the same way as above and the dyes thus prepared are shown in the same table together with the colors of gelatin films dyed with the dyes.

TABLE 1

| Dye No. | Starting Material Compounds Formula II + Formula III | Y | R | X$^-$ |
|---|---|---|---|---|
| I-1 | II-10 + III-5 | 4-⌬-SO$_3$K | —C$_2$H$_5$ | $^-$SO$_3$-⌬-CH$_3$ |
| L-2 | II-20 + III-2 | 4-CH$_3$ 5-CH$_3$ | —CH(CH$_2$)$_2$SO$_3^-$<br>   \|<br>   CH$_3$ | — |
| I-3 | II-40 + III-3 | — | —CH$_3$<br>—(CH$_2$)$_5$SO$_3^-$ | — |
| I-4 | II-11 + III-4 | 4-⌬ | | — |
| I-5 | II-8 + III-1 | — | —(CH$_2$)$_3$SO$_3^-$ | — |
| I-6 | II-26 + III-6 | 4-⌬-SO$_3$Na | —(CH$_2$)$_3$SO$_3^-$ | — |

| Dye No. | Starting Material Compounds Formula II + Formula III | q | B | R$_1$ | Color of Dyed Gelatin Film |
|---|---|---|---|---|---|
| I-1 | II-10 + III-5 | 1 | — | —N(CH$_3$)(CH$_2$CHCH$_2$SO$_3$Na)<br>               \|<br>              OH | Orange |
| L-2 | II-20 + III-2 | 1 | — | —N((CH$_2$)$_3$SO$_3$K)$_2$ | " |
| I-3 | II-40 + III-3 | 1 | — | —N((CH$_2$)$_3$SO$_3$K)((CH$_2$)$_2$OCOOC$_2$H$_5$) | " |
| I-4 | II-11 + III-4 | 1 | — | —N((CH$_2$)$_2$SO$_3^-$)(CH$_3$-⌬-CH$_3$, SO$_3$H) | Red |

TABLE 1-continued

| I-5 | II-8 + III-1 | 1 | 2-NHCOCH₃ 4-OCH₃ | $-N\begin{matrix}CH_3\\(CH_2)_2CHSO_3H\\|\\CH_3\end{matrix}$ | Orange |
| --- | --- | --- | --- | --- | --- |
| I-6 | II-26 + III-6 | 1 | 2-NHCO—⌬ | $-N\begin{matrix}CH_3\\|\\CH_2CHCOOH\\(CH_2)_3SO_3Na\end{matrix}$ | " |

EXAMPLE 2

Preparation of the dye having the following formula:

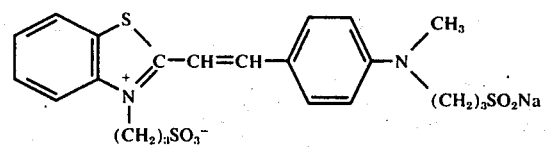

Dye No. I-7

30 g of Aldehyde Compound II-7, 4-(N-methyl-N-sulfopropyl)aminobenzaldehyde sodium salt and 25 g of Cyclic Quaternary Ammonium Salt III-7, 2-methyl-3-(3-sulfopropyl)benzthiazolium hydroxide intramolecular salt were dissolved in 120 ml of methanol and 5 ml of triethylamine was added to the solution. After refluxing the mixture for 25 minutes under heating, the reaction mixture was cooled and the dye precipitated was collected on a filter paper. By recrystallizing the dye thus collected from a mixture of 1 part of methanol and 3 parts of ethanol, 15 g of crystals of the dye was obtained. An aqueous solution of the dye had a red color and the absorption maximum wavelength thereof was 517 m$\mu$. $E_{max} = 4.1 \times 10^4$. The color of a gelatin film dyed with the dye is shown in the following table.

Various dyes having a benzothiazole nucleus were also prepared in the same way as described above and the dyes thus prepared are also shown in the same table together with the colors of gelatin films dyed with the dyes.

TABLE II

| Dye No. | Starting Material Compounds Formula II + Formula III | Y | R | X⁻ |
| --- | --- | --- | --- | --- |
| I-7 | II-7 + III-7 | — | —(CH₂)₃SO₃⁻ | — |
| I-8 | II-48 + III-8 | 6-CH₃ | —C₂H₅ | — |
| I-9 | II-27 + III-9 | 5-OH | —CH₂CH=CHSO₃⁻ | — |
| I-10 | II-21 + III-10 | 6-SO₃H | —(CH₂)₂COO⁻ | — |
| I-11 | II-47 + III-11 | 5-O(CH₂)₃SO₃H . N⌬ | $-CH(CH_2)_2COO^-$<br>$\mid$<br>$CH_3$ | — |
| I-12 | II-56 + III-11 | 5-O(CH₂)₃SO₃H | $-CH(CH_2)_2COO^-$<br>$\mid$<br>$CH_3$ | — |
| I-13 | II-36 + III-12 | 5-CH₃<br>6-SO₃K | —C₂H₅ | C₂H₅SO₄⁻ |
| I-14 | II-28 + III-13 | tetrahydro | —(CH₂)₂SO₃⁻ | — |

TABLE II-continued

[Structure 1: benzothiazolium with Y substituent, C-(CH=CH)-phenyl with B and R₁ substituents, X⁻ counterion, R on N]

[Structure 2: tetrahydrobenzothiazolium with R on N]

| Dye No. | Starting Material Compounds Formula II+ Formula III | q | B | R₁ | Color of Dyed Gelatin Film |
|---|---|---|---|---|---|
| I-7 | II-7 + III-7 | 1 | — | $-N(CH_3)(CH_2)_3SO_3Na$ | Orange |
| I-8 | II-48 + III-8 | 1 | — | $-O(CH_2)_2SO_3^-$ | Yellow |
| I-9 | II-27 + III-9 | 1 | 2-NHCOCH$_2$OH | $-N((CH_2)_2COOCH_3)((CH_2)_2CH(CH_3)SO_3H)$ | Orange |
| I-10 | II-21 + III-10 | 1 | 2-OCH$_3$ | $-N((CH_2)_2OH)((CH_2)_3SO_3H)$ | ″ |
| I-11 | II-47 + III-11 | 1 | — | $-N(COCH_3)(CH_2\text{-}C_6H_4\text{-}SO_3H \cdot N\text{-pyridine})$ | Yellow Orange |
| I-12 | II-56 + III-11 | 2 | — | $-O(CH_2)_3SO_3H$ | Red |
| I-13 | II-36 + III-12 | 1 | — | $-N((CH_2)_3NHCOCH_3)(CH_2CH(OH)CH_2SO_3K)$ | Orange Red |
| I-14 | II-28 + III-13 | 1 | — | $-N((CH_2)_2COCH_3)((CH_2)_3CH(C_2H_5)SO_3H)$ | ″ |

EXAMPLE 3

Preparation of the dye having the following formula:

Dye No. I-15

-continued

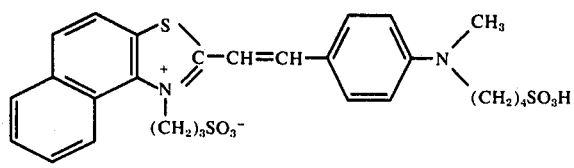

A mixture of 29 g of Aldehyde Compound II-9, 4-(N-methyl-N-4-sulfobutyl)aminobenzaldehyde, 33 g of Cyclic Quaternary Ammonium Salt III-14, 2-methyl-3-(3-sulfopropyl)naphtho[1,2-d]thiazolium hydroxide intramolecular salt, 1 ml of piperidine, and 250 ml of ethylene glycol monomethyl ether was refluxed for one hour under heating. The reaction mixture was cooled and then 300 ml of ethyl acetate was added to the reaction mixture to precipitate a dye, which was recovered by filtration. The dye was immersed overnight in acetone, filtered, dried, and recrystallized from ethanol to provide 21 g of crystals of the dye. An aqueous solution of the dye had a red color and the absorption maximum wavelength thereof was 524 m$\mu$. $E_{max} = 5.3 \times 10^4$. The color of a gelatin film dyed with the dye is shown in Table III.

Various dyes having a naphthothiazole nucleus were prepared in the same way as described above and the dyes thus prepared are shown in the same table together with the colors of gelatin films dyed with the dyes.

Dye No. I-19

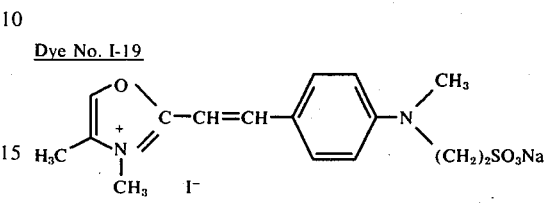

A mixture of 26.5 g of Aldehyde Compound II-6, 4-(N-methyl-N-sulfoethyl)aminobenzaldehyde sodium salt and 23.8 g of Cyclic Quaternary Ammonium Salt III-16, 2,3,4-trimethyloxazolium iodide was refluxed in 50 ml of glacial acetic acid for 25 minutes under heating. The reaction mixture was cooled and then ethyl acetate was added to the reaction mixture to form crystals, which were recovered by filtration. By recrystallizing the crystals from isopropanol, 20 g of crystals of the dye was obtained. An aqueous solution of the dye had a yellow color and the absorption maximum wavelength thereof was 450 m$\mu$. $E_{max} = 4.2 \times 10^4$. The color of a gelatin film dyed with the dye is shown in Table IV.

Various dyes having an oxazole nucleus were also prepared in the same way as described above and the dyes thus prepared and the color of gelatin films dyed with the dyes are also shown in the same table.

TABLE III

![structure]

| Dye No. | Starting Material Compounds Formula II + Formula III | Y | R | X⁻ | q | B | R₁ | Color of Dyed Gelatin Film |
|---|---|---|---|---|---|---|---|---|
| I-15 | II-9 + III-14 | — | —(CH₂)₃SO₃⁻ | — | 1 | — | —N(CH₃)(CH₂)₄SO₃H | Red |
| I-16 | II-24 + III-14 | — | —(CH₂)₃SO₃⁻ | — | 1 | — | —N(OH)(CH₂CHCH₂Cl) | " |
| I-17 | II-2 + III-15 | — | —CH₂CHCH₂CHSO₃⁻ (with two phenyl groups) | — | 1 | — | —N(H)((CH₂)₅SO₃H) | Orange Red |
| I-18 | II-37 + III-15 | — | —CH₂CHCH₂CHSO₃⁻ (with two phenyl groups) | — | 1 | — | —N((CH₂)₃SO₃H)((CH₂)₂NHSO₂CH₃), (CH₂)₂CHSO₃Ca/2 | Red |

EXAMPLE 4

Preparation of the dye having the following formula:

TABLE IV

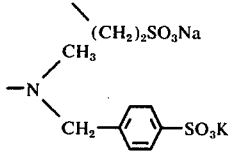

| Dye No. | Starting Material Compounds Formula II + Formula III | Y | R | X⁻ | q | B | $R_1$ | Color of Dyed Gelatin Film |
|---|---|---|---|---|---|---|---|---|
| I-19 | II-6 + III-16 | 4-CH₃ | —CH₃ | I⁻ | 1 | — | —N(CH₃)(CH₂)₂SO₃Na | Yellow |
| I-20 | II-12 + III-17 | 4-CH₃, 5-CH₃ | —(CH₂)₄COO⁻ | — | 1 | — | —N(CH₃)(CH₂-C₆H₄-SO₃K) | Yellow |

EXAMPLE 5

Preparation of the dye having the following formula:

Dye No. I-21

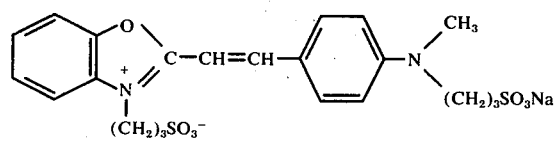

A mixture of 30 g of Aldehyde Compound II-7, 4-N-methyl-N-sulfopropyl)aminobenzaldehyde sodium salt, 24 g of Cyclic Quaternary Ammonium Salt III-18, 2-methyl-3-(3-sulfopropyl)benzoxazolium hydroxide intramolecular salt was dissolved in 150 ml of methanol and then 5 ml of piperidine was added to the solution. The mixture was refluxed for 45 minutes under heating. The reaction mixture was placed overnight in a refrigerator and the crystals precipitated were recovered by filtration and recrystallized from ethanol to provide 11 g of crystals of the dye. An aqueous solution of the dye had an orange color and the absorption maximum wavelength thereof was 494 m$\mu$. $E_{max} = 4.3 \times 10^4$.

EXAMPLE 6

Preparation of the dye having the following formula:

Dye No. I-22

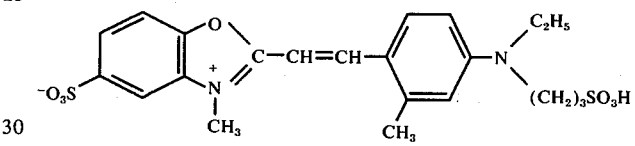

A mixture of 27 g of Aldehyde Compound II-13, 4-(N-ethyl-N-3-sulfopropyl)amino-2-methylbenzaldehyde, 17 g of Cyclic Quaternary Ammonium Salt III-23, 2,3-dimethyl-5-sulfobenzoxazolium iodine, and 250 ml of ethanol was mixed with 2 ml of pyridine and the resultant mixture was refluxed for 30 minutes under heating. The reaction mixture obtained was cooled and the crystals of the dye thus formed were recovered by filtration and recrystallized from methanol to provide 11 g of crystals of the dye. An aqueous solution of the dye had an orange color and the absorption maximum wavelength thereof was 509 m$\mu$. $E_{max} = 3.9 \times 10^4$.

The dyes prepared in Examples 5 and 6 and the colors of gelatin films dyed with those dyes are shown in the following table. Also, other similar dyes having a benzoxazole nucleus were prepared in the same manner as described in Examples 5 and 6 and the dyes thus prepared are shown in the same table together with the colors of gelatin films dyed with those dyes.

TABLE V

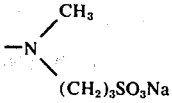

| Dye No. | Starting Material Compounds Formula II + Formula III | Y | R | X⁻ | q | B | $R_1$ | Color of Dyed Gelatin Film |
|---|---|---|---|---|---|---|---|---|
| I-21 | II-7 + III-18 | — | —(CH₂)₃SO₃⁻ | — | 1 | — | —N(CH₃)(CH₂)₃SO₃Na | Yellow Orange |

TABLE V-continued

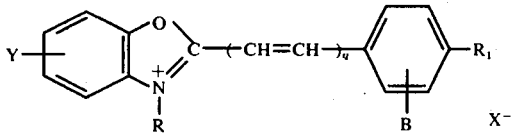

| Dye No. | Starting Material Compounds Formula II + Formula III | Y | R | X⁻ | q | B | R₁ | Color of Dyed Gelatin Film |
|---|---|---|---|---|---|---|---|---|
| I-22 | II-13 + III-23 | 5-SO₃⁻ | —CH₃ | — | 1 | 2-CH₃ | $-N\begin{array}{l}C_2H_5\\(CH_2)_2SO_3H\end{array}$ | Orange |
| I-23 | II-45 + III-18 | — | —(CH₂)₃SO₃⁻ | — | 1 | — | $-N\begin{array}{l}H\\\text{cyclohexyl}\end{array}$ | Orange Yellow |
| I-24 | II-1 + III-19 | — | —(CH₂)₂CHSO₃⁻<br>       \|<br>      CH₃ | — | 1 | — | $-N\begin{array}{l}H\\(CH_2)_3SO_3H\end{array}$ | " |
| I-25 | II-3 + III-20 | 5-CH₃ | —C₄H₉ | — | 1 | 2-CH₃ | $-N\begin{array}{l}H\\(CH_2)_2SO_3H\end{array}$ | Yellow Orange |
| I-26 | II-29 + III-21 | 5-Cl | —(CH₂)₄SO₃⁻ | — | 1 | — | $-N\begin{array}{l}(CH_2)_3SO_3^-\\(CH_2)_2OCOCH_3\end{array}$ | Orange Red |
| I-27 | II-23 + III-22 | 4-CH₃<br>6-CH₃ | —CH₂CHCH₂SO₃⁻<br>         \|<br>         OH | — | 1 | — | $-N\begin{array}{l}\text{(phenyl-CH}_2\text{-SO}_3H)\\CH_2\end{array}$ | Orange Yellow |
| I-28 | II-28 + II-23 | 5-SO₃⁻ | CH₃ | — | 1 | 3-COOH | $-N\begin{array}{l}(CH_2)_2Cl\\CH_2CHCH_2SO_3H\\\quad\ \|\\\quad OH\end{array}$ | Yellow Orange |
| I-29 | II-55 + III-23 | 5-SO₃⁻ | CH₃ | — | 2 | — | $-N\begin{array}{l}(CH_3)_3OSO_3CH_3\\(CH_2)_2-\text{phenyl-SO}_3H\end{array}$ | Purple Red |
| I-30 | II-50 + III-24 | 5-SO₃H·N(C₂H₅)₃ | —(CH₂)₂COO⁻ | — | 1 | 3-COOK | $-N\begin{array}{l}(CH_2)_2OH\\(CH_2)_2SO_3H\end{array}$<br>—O(CH₂)₃CHSO₃K<br>              \|<br>              CH₃ | Yellow |
| I-31 | II-44 + III-24 | 5-SO₃Ca/2 | —(CH₂)₂COO⁻ | — | 1 | 2-NHCOOC₂H₅ | $-N\begin{array}{l}\text{phenyl}\\(CH_2)_2SO_3Ca/2\end{array}$ | Orange Red |
| I-32 | II-30 + III-25 | 5-SO₃H | —(CH₂)₃SO₃⁻ | — | 1 | — | $-N\begin{array}{l}(CH_2)_2OCO\text{-phenyl}\\CH_2CHCH_2SO_3H\\\quad\ \|\\\quad OH\end{array}$ | Yellow Orange |

EXAMPLE 7

Preparation of the dye having the following formula:

Dye No. I-33

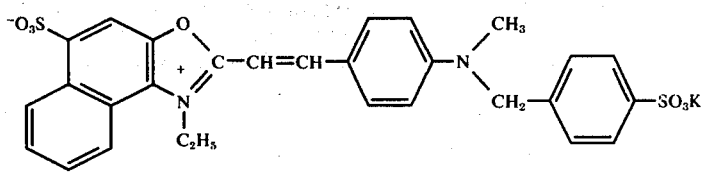

33 g of Aldehyde Compound II-12, 4-[N-methyl-N-(p-sulfobenzyl)]aminobenzaldehyde potassium salt and 38 g of Cyclic Quaternary Ammonium Salt III-27, 2-methyl-3-ethyl-8-sulfonaphtho[1,2-d]oxazolium ethylsulfate were dissolved in 200 ml of methanol and after adding 1 ml of piperidine to the solution, the mixture was refluxed for 25 minutes under heating. The reaction mixture was quickly cooled and crystals of the dye thus formed were recovered by filtration, washed with acetone, dried, and then recrystallized from ethanol to provide 17 g of orange-red crystals of the dye. An aqueous solution of the dye had a orange-red color and the absorption maximum wavelength thereof was 513 m$\mu$. $E_{max} = 4.6 \times 10^4$. The color of a gelatin film dyed with the dye is shown in the following table.

Other similar dyes having a naphthoxazole nucleus were also prepared in the same way as described above and the dyes thus prepared are shown in the same table together with the colors of gelatin films dyed with the dyes.

TABLE VI

| Dye No. | Starting Material Compounds Formula II + Formula III | Y | R | X⁻ | q | B | R₁ | Color of Dyed Gelatin Film |
|---|---|---|---|---|---|---|---|---|
| I-33 | II-12 + III-27 | 8-SO₃⁻ | —C₂H₅ | — | 1 | — | —N(CH₃)(CH₂—C₆H₄—SO₃K) | Orange Red |
| I-34 | II-19 + III-26 | — | —(CH₂)₃SO₃⁻ | — | 1 | — | —N((CH₂)₂CN)((CH₂)₂SO₃H) | " |
| I-35 | II-39 + III-26 | — | —(CH₂)₃SO₃⁻ | — | 1 | 2-NO₂ | —N((CH₂)₂SC₂H₅)(CH₂CH(C₆H₅)CH₂CH(C₆H₅)SO₃H) | Red Orange |
| I-36 | II-35 + III-27 | 8-SO₃⁻ | —C₂H₅ | — | 1 | 2-C₂H₅ | —N((CH₂)₂N(CH₃)(C₆H₅))((CH₂)₃SO₃H) | Orange Red |
| I-37 | II-4 + III-28 | 8-SO₃Na | —(CH₂)₄SO₃⁻ | — | 1 | — | —N(H)((CH₂)₂CH(SO₃Na)CHO) | Red Orange |
| I-38 | II-46 + III-28 | 8-SO₃H | —(CH₂)₄SO₃⁻ | — | 1 | 2-NHCOCH₂Cl | —N(SO₂—C₆H₄—CH₃)((CH₂)₂SO₃H) | Orange Red |

EXAMPLE 8

Preparation of the dye having the following formula:

Dye No. I-39

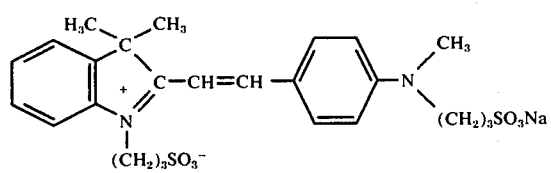

7.7 g of Cyclic Quaternary Ammonium Salt III-29, 2,3,3-trimethyl-1-(3-sulfopropyl)indolenium hydroxide intramolecular salt was added to 30 ml of methanol and then 2 g of triethylamine was added thereto. Then, a solution of 5.3 g of Aldehyde Compound II-7, 4-N-methyl-N-(3-sulfopropyl)aminobenzaldehyde potassium salt in 15 ml of water was added to the above mixture and after further adding thereto 3 ml of glacial acetic acid, the resultant mixture was refluxed for 1 hour under heating. The reaction mixture was allowed to stand overnight and then the reaction mixture was added to 150 ml of isopropanol with stirring to form crystals of the dye, which were recovered by filtration and recrystallized from a mixture of 10 ml of water and 23 ml of isopropanol and then from a mixture of 25 ml of methanol and 5 ml of isopropanol to provide 3.7 g of crystals of the dye. An aqueous solution of the dye had a purple-red color and the abosrption maximum wavelength thereof was 542 m$\mu$. $E_{max} = 7.3 \times 10^4$.

EXAMPLE 9

Preparation of the dye having the following formula:

Dye No. I-40

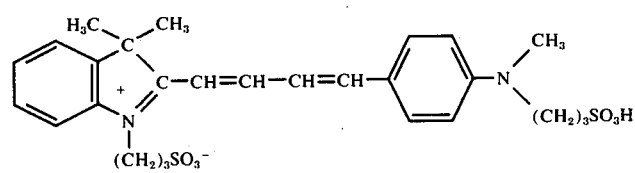

6.2 g of Aldehyde Compound II-52, 4-(N-methyl-N-sulfopropyl)aminocinnamaldehyde and 6 g of Cyclic Quaternary Ammonium Salt III-29, 2,3,3-trimethyl-1-(3-sulfopropyl)indolenium hydroxide intramolecular salt were added to 70 ml of methanol and after adding thereto 0.5 ml of piperidine, the mixture was refluxed for one hour and 20 minutes under heating. The reaction mixture was cooled and 200 ml of ethyl acetate was added to the reaction mixture with stirring to precipitate the dye. The crystals of the dye were recovered by filtration and recrystallized from methanol to provide 2.7 g of crystals of the dye. An aqueous solution of the dye had a green-blue color and the maximum absorption wavelength thereof was 630 m$\mu$. $E_{max} = 6.2 \times 10^4$.

EXAMPLE 10

Preparation of the dye having the following formula:

Dye No. I-42

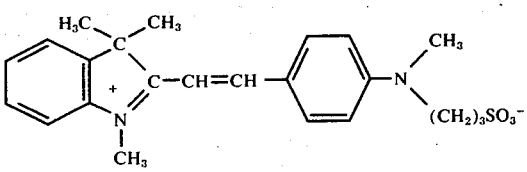

39 g of Aldehyde Compound II-6, 4-(N-methyl-N-sulfoethyl)aminobenzaldehyde sodium salt and 42 g of Cyclic Quaternary Ammonium Salt III-30, 1,2,3,3-tetramethylindolenium bromide were dissolved in a mixture of 15 g of triethylamine and 150 ml of methanol under heating and after further adding thereto 18 ml of glacial acetic acid, the resultant mixture was refluxed for 2 hours on a water bath. Then, the solvents were distilled off from the reaction mixture and 500 ml of water was added to the residue followed by stirring under heating. The crystals of the dye thus formed were recovered by filtration, washed well with acetone, and recrystallized from a mixture of 10 parts of methanol and 3 parts of isopropanol to provide 39 g of crystals of the dye. The methanol solution of the dye had a red color and the maximum absorption wavelength thereof was 541 m$\mu$. $E_{max} = 9.1 \times 10^4$.

The dyes and the colors of gelatin films dyed with the dyes prepared in Examples 8, 9 and 10 are shown in the following table together with dyes having an indole nucleus prepared in the same manner as described in the aforesaid examples and the colors of gelatin films dyed with the dyes.

TABLE VII

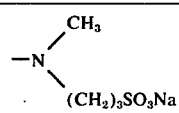

| Dye No. | Starting Compounds Formula II + Formula III | Y | R | R₂, R₃ | X⁻ | q | B | R₁ | Color of Dyed Gelatin Film |
|---|---|---|---|---|---|---|---|---|---|
| I-39 | II-7 + III-29 | — | $-(CH_2)_3SO_3^-$ | $-CH_3$ <br> $-CH_3$ | — | 1 | — | $-N\begin{matrix}CH_3\\(CH_2)_3SO_3Na\end{matrix}$ | Red |
| I-40 | II-54 + III-29 | — | $-(CH_2)_3SO_3^-$ | $-CH_3$ <br> $-CH_3$ | — | 2 | — | $-N\begin{matrix}CH_3\\(CH_2)_2SO_3H\end{matrix}$ | Purple |
| I-41 | II-18 + III-29 | — | $-(CH_2)_3SO_3^-$ | $-CH_3$ <br> $-CH_3$ | — | 1 | — | $-N\begin{matrix}C_{12}H_{25}\\(CH_2)_2SO_3H \cdot N(C_2H_3)_3\end{matrix}$ | Red |
| I-42 | II-6 + III-30 | — | $-CH_3$ | $-CH_3$ <br> $-CH_3$ | — | 1 | — | $-N\begin{matrix}CH_3\\(CH_2)_2SO_3^-\end{matrix}$ | " |
| I-43 | II-51 + III-31 | — | $-(CH_2)_2SO_3^-$ | $-CH_3$ <br> $-CH_3$ | — | 1 | 2-CH₃ | $-OCH_2CH(OH)-CH_2SO_3Na$ | Orange Yellow |
| I-44 | II-33 + III-31 | — | $-(CH_2)_2SO_3^-$ | $-CH_3$ <br> $-CH_3$ | — | 1 | — | $-N\begin{matrix}(CH_2)_2O(CH_2)_2CN\\(CH_2)_2SO_3H\end{matrix}$ | Red |
| I-45 | II-43 + III-32 | 5-Cl | $-CH_2CH(OH)CH_2SO_3^-$ | $-CH_3$ <br> $-CH_3$ | — | 1 | — | $-N\begin{matrix}(CH_2)_2-\text{Ph}-CH_3\\CH_2-CH=CHSO_3H\end{matrix}$ | Orange |
| I-46 | II-5 + III-33 | 5-OCH₃ | $-(CH_2)_2SO_3^-$ | $-C_2H_5$ <br> $-C_2H_5$ | — | 1 | — | $-N\begin{matrix}H\\(CH_2)_2-\text{Ph}-SO_3H\end{matrix}$ | " |
| I-47 | II-34 + III-34 | 5-NO₂ | $-(CH_2)_3SO_3^-$ | $-CH_3$ <br> $-C_2H_5$ | — | 1 | 2-OC₂H₅ | $-N\begin{matrix}(CH_2)_2N(CH_3)_2\\(CH_2)_3SO_3H\end{matrix}$ | Red |
| I-48 | II-42 + III-35 | 5-COOC₂H₅ | $-(CH_2)_3\underset{C_2H_5}{CH}SO_3^-$ | $-CH_3$ <br> $-CH_3$ | — | 1 | — | $-N\begin{matrix}CH_2-\text{Ph}-OCH_3\\CF_2-CF_2SO_3H\end{matrix}$ | " |
| I-49 | II-17 + III-36 | 5-C₃H₇ | $-CF_2CF_2SO_3^-$ | $-CH_3$ <br> $-CH_3$ | — | 1 | 2-NHCOC₂H₅ | $-N\begin{matrix}C_4H_9\\(CH_2)_3SO_3H\end{matrix}$ | " |
| I-50 | II-15 + III-37 | 5-OCH₃ | $-(CH_2)_3SO_3^-$ | $-CH_3$ <br> $-(CH_2)_2N(CH_3)_2$ | — | 1 | — | $-N\begin{matrix}C_2H_5\\CH_2CH=CHSO_3K\end{matrix}$ | Red |

TABLE VII-continued

| Dye No. | Starting Compounds Formula II + Formula III | Y | R | R₂, R₃ | X⁻ | q | B | R₁ | Color of Dyed Gelatin Film |
|---|---|---|---|---|---|---|---|---|---|
| I-51 | II-32 + III-38 | 5-CH₃ | —C₄H₉ | —CH₃<br>—(CH₂)₂O—⌬ | Br⁻ | 1 | 2-F | —N(CH₂)₂O—⌬ / CH₂—CH=CHSO₃H | Orange |
| I-52 | II-25 + III-39 | — | —CH₂CH=CHSO₃⁻ | —CH₃<br>—CH₃ | — | 1 | — | —N(CH₂)₂COOH / (CH₂)₂SO₃H | Red |

EXAMPLE 11

Preparation of the dye having the following formula:

Dye No. I-53

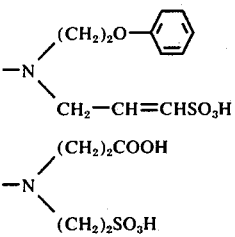

3.2 g of Aldehyde Compound II-14, 4-[N-ethyl-N-(1-methyl-4-sulfobutyl]aminobenzaldehyde and 3 g of Cyclic Quaternary Ammonium Salt III-40, 2,3,3-trimethyl-1-ethyl-1H-benzindolium thiocyanate sulfonate were dissolved in a mixture of 50 ml of methanol and 1 ml of pyridine and the solution was refluxed for 35 minutes under heating. The crystals of the dye thus formed were recovered by filtration, washed with acetone, dried, and recrystallized from acetic acid to provide 2.3 g of crystals of the dye. An aqueous solution of the dye had a purple-red color and the maximum absorption wavelength thereof was 572 m$\mu$. $E_{max} = 5.7 \times 10^4$.

EXAMPLE 12

Preparation of the dye having the following formula:

Dye No. I-54

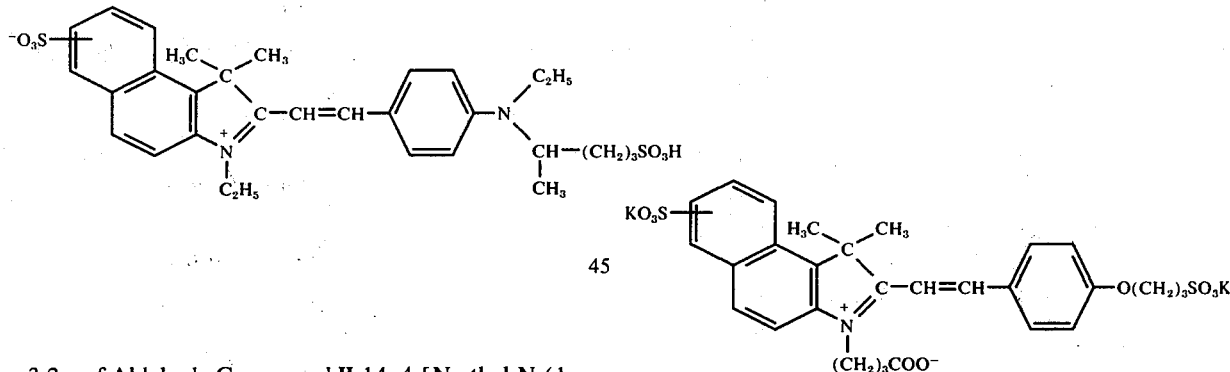

2.7 g of Aldehyde Compound II-49, 4-(3-sulfopropyl)oxybenzaldehyde potassium salt and 3.8 g of Cyclic Quaternary Ammonium Salt III-41, 2,3,3-trimethyl-1-(3-carboxypropyl)-1H-benzindolium hydroxide sulfonate were added to 70 ml of methanol, and after adding thereto 1 ml of pyridine, the resultant mixture was refluxed for 50 minutes under heating. A solution of 2 g of potassium acetate in 10 ml of methanol was added to the reaction mixture thus obtained and the mixture was further heated for 5 minutes. The reaction mixture was cooled and crystals of the dye thus formed were recovered by filtration, washed with ethanol, dried, and recrystallized from methanol to provide 1.5 g of crystals of the dye. An aqueous solution of the dye had an orange-yellow color and the maximum absorption wavelength thereof was 464 m$\mu$. $E_{max} = 5.2 \times 10^4$.

The colors of the gelatin films dyed with the dyes prepared in Examples 11 and 12 are shown in the following table. Also, other similar dyes having a benzoindole nucleus were prepared in the same manner as described in Examples 11 and 12 and the dyes thus prepared are shown in the same table together with the colors of gelatin films dyed with the dyes.

Cyclic Quaternary Ammonium Salt III-43, 2,4-dimethyl-3-butylselenazolium iodide were added to a mixture of 2.5 g of triethylamine and 100 ml of methanol and the mixture was refluxed for 2 hours on a water bath. The solvents were distilled off from the reaction mix-

TABLE VIII

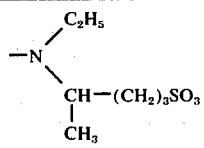

| Dye No. | Starting Material Compounds Formula II + Formula III | Y | R | $R_2, R_3$ | $X^-$ | q | B | $R_1$ | Color of Dyed Gelatin Film |
|---|---|---|---|---|---|---|---|---|---|
| I-53 | II-14 + II-40 | —SO$_3^-$ | —C$_2$H$_5$ | —CH$_3$<br>—CH$_3$ | — | 1 | 2-Cl | 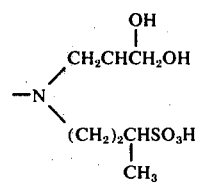 | Purple Red |
| I-54 | II-49 + III-41 | —SO$_3$K | —(CH$_2$)$_3$COO$^-$ | —CH$_3$<br>—CH$_3$ | — | 1 | — | —O(CH$_2$)$_3$SO$_3$K | Orange Yellow |
| I-55 | II-22 + III-40 | —SO$_3^-$ | —C$_2$H$_5$ | —CH$_3$<br>—CH$_3$ | — | 1 | 2-OH | 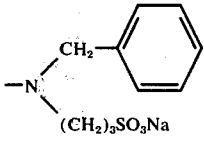 | Red |
| I-56 | II-41 + III-41 | —SO$_3$Na | —(CH$_2$)$_3$COO$^-$ | —CH$_3$<br>—CH$_3$ | — | 1 | 2-NHSO$_2$C$_2$H$_5$ | 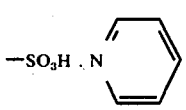 | Purple Red |
| I-57 | II-16 + III-42 | 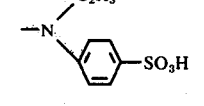 | —(CH$_2$)$_3$SO$_3^-$ | —CH$_3$<br>—CH$_3$ | — | 1 | — | 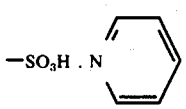 | Purple |
| I-58 | II-31 + III-42 | 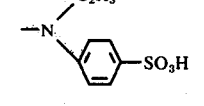 | —(CH$_2$)$_3$SO$_3^-$ | —CH$_3$<br>—CH$_3$ | — | 1 | 3-SCH$_3$ | 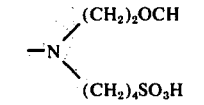 | Red |

EXAMPLE 13

Preparation of the dye having the following formula:

Dye No. I-59

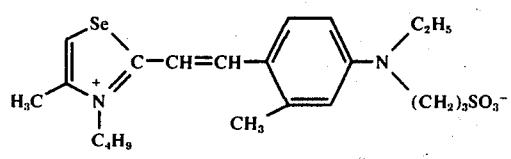

5.1 g of Aldehyde Compound II-13, 4-N-ethyl-N-(3-sulfopropyl)amino-2-methylbenzaldehyde and 6.9 g of ture, 70 ml of water was added to the residue, and the mixture was heated with stirring. The crystals of the dye formed were recovered by filtration, washed well with acetone, and recrystallized from a mixture of 1 part of methanol and 1 part of isopropanol to provide 6.0 g of crystals of the dye. A methanol solution of the dye had an orange color and the maximum absorption wavelength thereof was 485 m$\mu$. $E_{max} = 4.8 \times 10^4$.

EXAMPLE 14

Preparation of the dye having the following formula:

Dye No. I-60

-continued

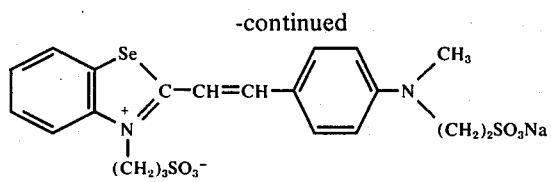

A solution of 7.9 g of Aldehyde Compound II-6, 4-N-methyl-N-β-sulfoethylaminobenzaldehyde sodium salt in 20 ml of water was added to a solution of 9.5 g of Cyclic Quaternary Ammonium Salt III-44, 2-methyl-3-(3-sulfopropyl)benzselenazolium hydroxide intramolecular salt in 3 g of triethylamine and 100 ml of methanol and then the mixture was refluxed for 3 hours under heating. Then, the reaction mixture was added to 300 ml of isopropanol with stirring and crystals of the dye thus formed were recovered by filtration and recrystallized from a mixture of 1 part of water and 3 parts of isopropanol to provide 5.8 g of crystals of the dye. An aqueous solution of the dye had a red color and the absorption maximum wavelength thereof was 529 mμ. $E_{max} = 4.0 \times 10^4$.

Also, other similar dyes having a benzoselenazole nucleus were prepared in the same manner as described above and the dyes thus prepared are shown in the following table together with the colors of gelatin films dyed with the dyes.

EXAMPLE 15

Preparation of the dye having the following formula:

Dye No. I-63

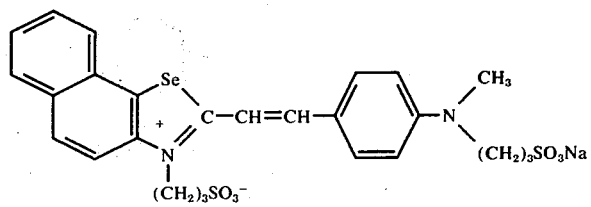

5.3 g of Aldehyde Compound II-6, 4-N-methyl-N-(β-sulfoethyl)aminobenzaldehyde sodium salt was dissolved in 10 ml of water and the solution was added to a solution of 7.3 g of Cyclic Quaternary Ammonium Salt III-47, 2-methyl-3-(3-sulfopentyl)naphtho[2,1-d]thiazolium hydroxide intramolecular salt in 2.2 g of triethylamine and 100 ml of methanol and the mixture was refluxed for 2.5 hours under heating. The reaction mixture was added to 300 ml of isopropanol with stirring and crystals of the dye formed were recovered by filtration and recrystallized from a mixture of 1 part of water and 4 parts of isopropanol to provide 4.9 g of crystals of the dye. An aqueous solution of the dye had a red color and the absorption maximum wavelength was 536 mμ. $E_{max} = 4.7 \times 10^4$.

EXAMPLE 16

Preparation of the dye having the following formula:

Dye No. I-64

TABLE IX

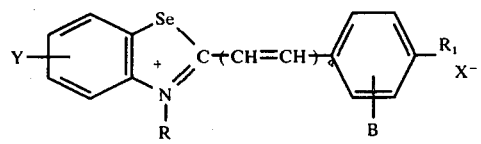

| Dye No. | Starting Material Compounds Formula II + Formula II | Y | R | X⁻ | q | B | R₁ | Color of Dyed Gelatin Film |
|---|---|---|---|---|---|---|---|---|
| I-60 | II-6 + III-44 | — | —(CH₂)₃SO₃⁻ | — | 1 | — | —N(CH₃)(CH₂)₂SO₃Na | |
| I-61 | II-52 + III-45 | 5-Cl | —CH(CH₂)₂SO₃⁻<br>\|<br>CH₃ | — | 1 | 3-O(CH₂)₃SO₃K | —O(CH₂)₃SO₃K | |
| I-62 | II-25 + III-46 | 5-OCH₃ | —(CH₂)₂COO⁻ | — | 1 | — | —N((CH₂)₂COOH)((CH₂)₂SO₃H) | |

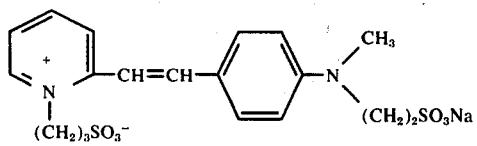

6.2 g of Cyclic Quaternary Ammonium Salt III-49, 2-methyl-1-(3-sulfopropyl)pyridinium hydroxide intromolecular salt was added to 80 ml of methanol and then 13.0 ml of triethylamine was further added to the mixture. Thereafter, a solution of Aldehyde Compound II-6, 4-N-methyl-N-(β-sulfoethyl)aminobenzaldehyde sodium salt in 20 ml of water was added to the mixture prepared above and the mixture was refluxed for 2 hours under heating and allowed to stand overnight. Crystals of the dye thus prepared were recovered by filtration and recrystallized from a mixture of 1 part of water and 3 parts of methanol to provide 6.1 g of crystals of the dye. An aqueous solution of the dye had a yellow color and the absorption maximum wavelength was 431 mμ. $E_{max} = 3.6 \times 10^4$. the color of a gelatin film dyed with the dye is shown in the following table.

other similar dyes prepared in the same manner as described above are also shown in the same table together with the colors of gelatin films dyed with the dyes.

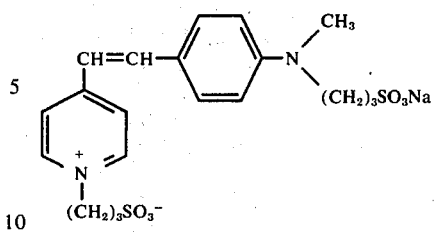

6.2 g of Cyclic Quaternary Ammonium Salt III-50, 4-methyl-1-(3-sulfopropyl)pyridinium hydroxide intramolecular salt was added to 80 ml of methanol and then 13 ml of triethylamine was further added to the mixture. Thereafter, a solution of 7.9 g of Aldehyde Compound II-7, 4-N-methyl-N-(3-sulfopropyl)aminobenzaldehyde sodium salt in 20 ml of water was added to the mixture and the resultant mixture was refluxed for 2 hours under heating overnight. Crystals of the dye formed were recovered by filtration and recrystallized from a mixture of 1 part of water and 3 parts of methanol to provide 5.7 g of crystals of the dye. An aqueous solution of the dye had a yellow color and the absorption maximum wavelength thereof was 455 mμ. $E_{max} = 3.7 \times 10^4$.

EXAMPLE 18

TABLE X

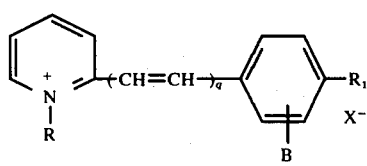

| Dye No. | Starting Material Compounds Formula II + Formula III | R | X⁻ | q | B | R₁ | Color of Dyed Gelatin Film |
|---|---|---|---|---|---|---|---|
| I-64 | II-6 + III-49 | —(CH₂)₃SO₃⁻ | — | 1 | — | —N(CH₃)(CH₂)₂SO₃Na | Yellow |
| I-65 | II-53 + III-48 | —C₂H₅ | I⁻ | 1 | 2-O(CH₂)₃SO₃K | —O(CH₂)₃SO₃K | Yellow |
| I-66 | II-35 + III-49 | —(CH₂)₃SO₃⁻ | — | 1 | 2-C₂H₅ | —N(CH₃)((CH₂)₂N(C₆H₅)(CH₂)₃SO₃H) | Yellow |

EXAMPLE 17

Preparation of the dye having the following formula:

Dye No. I-67

Preparation of the dye having the following formula:

Dye No. I-68

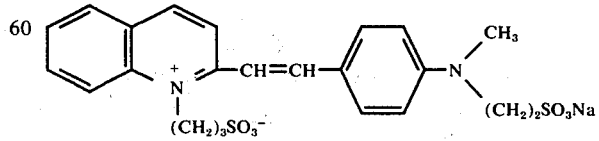

7.9 g of Cyclic Quaternary Ammonium Salt III-51, 2-methyl-1-(3-sulfopropyl)quinolinium hydroxide and intramolecular salt was dissolved in a mixture of 10 ml of triethylamine and 80 ml of methanol and then a solution of 7.9 g of Aldehyde Compound II-6, 4N-methyl-N-(β-sulfoethyl)aminobenzaldehyde sodium salt in 20 ml of water was added to the solution. The mixture was refluxed for one hour under heating and allowed to stand for 14 hours at room temperature (about 20°–30° C), whereby crystals were precipitated. The crystals were recovered by filtration, washed with acetone and ethanol, and recrystallized from a mixture of 1 part of water and 2 parts of ethanol to provide 5.8 g of crystals of the dye. An aqueous solution of the dye had a red color and the absorption maximum wavelength thereof was 499 mμ. $E_{max} = 3.7 \times 10^4$.

EXAMPLE 19

Preparation of the dye having the following formula:

Dye No. I-69 then 6 g of triethylamine was added to the mixture. Thereafter, a solution of 8.4 g of Aldehyde Compound II-49, 4-(3-sulfopropyl)oxybenzaldehyde potassium salt in 10 ml of water was added to the mixture. The resultant mixture was refluxed for one hour under heating and allowed to stand for 14 hours at room temperature, whereby crystals of the dye formed were precipitated. The crystals were recovered by filtration, washed with acetone and ethanol, and then recrystallized from a mixture of 1 part of water and 2 parts of ethanol to provide 4.3 g of crystals of the dye. An aqueous solution of the dye had yellow color and the maximum absorption wavelength was 409 mμ. $E_{max} = 3.2 \times 10^4$.

The colors of gelatin films dyed with the dyes prepared in Examples 18 and 19 are shown in the following table.

Other similar dyes having a quinoline nucleus prepared in the same manner as described in Examples 18 and 19 are also shown in the same table together with the colors of gelatin films dyed with the dyes.

TABLE XI

| Dye No. | Starting Material Compounds Formula II + Formula III | Y | R | X⁻ | q | B | R₁ | Color of Dyed Gelatin Film |
|---|---|---|---|---|---|---|---|---|
| I-68 | II-6 + III-51 | — | —(CH₂)₃SO₃⁻ | — | 1 | — | —N(CH₃)(CH₂)₂SO₃Na | Red |
| I-69 | II-49 + III-51 | — | —(CH₂)₃SO₃⁻ | — | 1 | — | —O(CH₂)₃SO₃K | Yellow |
| I-70 | II-55 + III-51 | — | —(CH₂)₃SO₃⁻ | — | 1 | — | —N((CH₂)₂OH)((CH₂)₂SO₃⁻) | Blue Purple |
| I-71 | II-29 + III-53 | 5-C₂H₅ | —(CH₂)₂COO⁻ | — | 1 | — | —N((CH₂)₂OCOCH₃)(C₆H₃(CH₃)(SO₃H)) | Purple Red |
| I-72 | II-50 + III-53 | 5-C₂H₅ | —(CH₂)₂COO⁻ | — | 1 | 3-COOK | —O(CH₂)₃CH(CH₃)—SO₃K | Yellow |
| I-73 | II-45 + III-54 | 8-OC₂H₅ | —CH₃ | — | 1 | — | —N(C₆H₁₁)((CH₂)₃SO₃⁻) | Red |

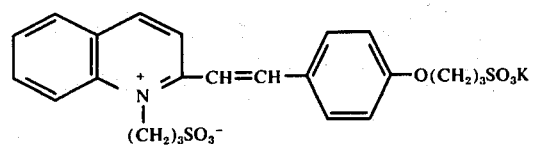

7.9 g of Cyclic Quaternary Ammonium Salt III-51, 2-methyl-1-(3-sulfopropyl)quinolinium hydroxide intramolecular salt was added to 100 ml of methanol and

EXAMPLE 20

Preparation of the dye having the following formula:

Dye No. I-74

-continued

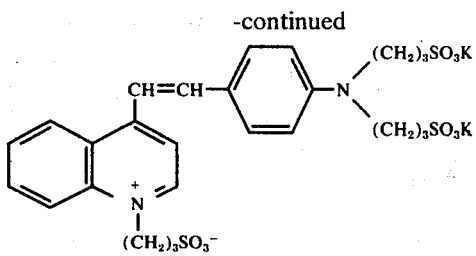

7.9 g of Cyclic Quaternary Ammonium Salt III-52, 4-methyl-1-(3-sulfopropyl)quinolinium hydroxide intramolecular salt was added to 100 ml of methanol and then 6 g of triethylamine was added to the mixture. Thereafter, a solution of 12.7 g of Aldehyde Compound II-20, 4-N,N-di(3-sulfopropyl)aminobenzaldehyde potassium salt in 15 ml of water was added to the mixture and the resultant mixture was refluxed for 1 hour under heating and the reaction mixture was allowed to stand for 14 hours at room temperature, whereby crystals of the dye were precipitated. The crystals were recovered by filtration, washed with acetone and ethanol, and recrystallized from a mixture of 1 part of water and 2 parts of ethanol to provide 7.5 g of crystals of the dye. An aqueous solution of the dye had a red color and the maximum absorption wavelength thereof was 515 m$\mu$. $E_{max} = 3.8 \times 10^4$. The color of a gelatin film dyed with the dye is shown in the following table.

Other similar dyes having a quinoline nucleus were also prepared in the manner as described above and the dyes thus prepared and the colors of gelatin films dyed with the dyes are also shown in the same table.

EXAMPLE 21

Preparation of the dye having the following formula:

Dye No. I-77

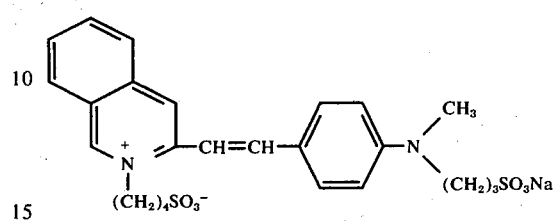

A mixture of 8 g of Aldehyde Compound II-7, 4N-methyl-N-(3-sulfopropyl)aminobenzaldehyde sodium salt, 6 g of Cyclic Quaternary Ammonium Salt III-55, 3-methyl-2-(4-sulfobutyl)isoquinolinium hydroxide intramolecular salt, 100 ml of methanol, and 2 ml of piperidine was refluxed for 1 hour under heating. The reaction mixture was allowed to stand for 12 hours and crystals of the dye formed were recovered by filtration, washed with acetone and ethanol, and recrystallized from a mixture of 1 part of water and 2 parts of methanol to provide 6.0 g of crystals of the dye. An aqueous solution of the dye had a red color and the maximum absorption wavelength thereof was 499 m $\mu$. $E_{max} = 3.5 \times 10^4$. The color of a gelatin film dyed with the dye is shown in the following table.

Other similar dyes having an isoquinoline nucleus were also prepared in the manner as described in the above process and the dyes thus prepared are shown in the same table together with the colors of gelatin films dyed with the dyes.

TABLE XII

| Dye No. | Starting Material Compounds Formula II + Formula III | R | X$^-$ | q | B | R$_1$ | Color of Dyed Gelatin Film |
|---|---|---|---|---|---|---|---|
| I-74 | II-20 + III-52 | —(CH$_2$)$_3$SO$_3^-$ | — | 1 | — | —N((CH$_2$)$_3$SO$_3$K)((CH$_2$)SO$_3$K) | Red |
| I-75 | II-49 + III-52 | —(CH$_2$)$_3$SO$_3^-$ | — | 1 | — | —O(CH$_2$)$_3$SO$_3$K | Yellow |
| I-76 | II-55 + III-52 | —(CH$_2$)$_3$SO$_3^-$ | — | 2 | — | —N((CH$_3$)$_3$OH)((CH$_2$)$_2$SO$_3$H) | Purple Blue |

TABLE XIII

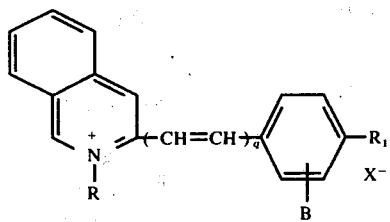

| Dye No. | Starting Material Compounds Formula II + Formula III | R | X⁻ | q | B | R₁ | Color of Dyed Gelatin Film |
|---|---|---|---|---|---|---|---|
| I-77 | II-7 + III-55 | —(CH₂)₄SO₃⁻ | — | 1 | — | —N(CH₃)(CH₂)₃SO₃Na | Red |
| I-78 | II-50 + III-55 | —(CH₂)₄SO₃⁻ | — | 1 | 3-COOK | —O(CH₂)₃CH(CH₃)SO₃K | Yellow |
| I-79 | II-44 + III-55 | —(CH₂)₄SO₃⁻ | — | 1 | 2-NHCOOC₂H₅ | —N(C₆H₅)(CH₂)₂SO₃H | Purple Blue |

EXAMPLE 22

Preparation of the dye having the following formula:

Dye No. I-80

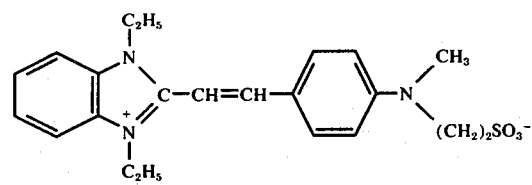

4.5 g of Aldehyde Compound II-6, 4-N-methyl-N-(β-sulfoethyl)aminobenzaldehyde and 6.2 g of Cyclic Quaternary Ammonium Salt III-56, 1,3-diethyl-2-methylbenzimidazolium iodide were added to a mixture of 70 ml of pyridine and 3 ml of piperidine and the mixture was refluxed for 2 hours under heating. The reaction mixture was allowed to stand for 16 hours at room temperature and the crystals of the dye formed were recovered by filtration, washed with water and acetone and then recrystallized from a mixture of 1 part of water and 5 parts of methanol to provide 3.9 g of crystals of the dye. A methanol solution of the dye had a yellow-orange color and the maximum absorption wavelength was 412 mμ. $E_{max} = 3.9 \times 10^4$.

EXAMPLE 23

Preparation of the dye having the following formula:

Dye No. I-81

-continued

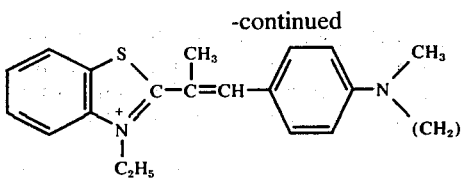

8.3 g of Aldehyde Compound II-7, 4-N-methyl-N-(3-sulfopropyl)aminobenzaldehyde sodium salt and 5.7 g of Cyclic Quaternary Ammonium Salt III-57, 2,3-diethylbenzthiazolium iodide were added to 30 ml of glacial acetic acid and the mixture was refluxed for 1 hour under heating. The reaction mixture was poured in 100 ml of water, heated for a few hours, and cooled. The crystals of the dye formed were recovered by filtration, washed with water and acetone, and then recrystallized from a mixture of 1 part of water and 4 parts of methanol to provide 4.2 g of crystals of the dye. A methanol solution of the dye had a red color and the maximum absorption wavelength thereof was 454 mμ. $E_{max} = 4.1 \times 10^4$.

EXAMPLE 24

Preparation of the dye having the following formula:

Dye No. I-82

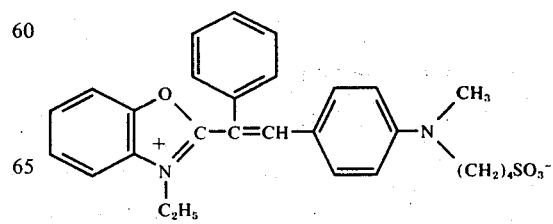

2.9 g of Aldehyde Compound II-9, 4N-methyl-N-(β-sulfobutyl)aminobenzaldehyde and 2.2 g of Cyclic Quaternary Ammonium Salt III-60, 2-benzyl-1-ethyl-benzoxazolium iodide were added to a mixture of 10 ml of methanol and 0.2 g of triethylamine and the mixture was refluxed for 4 hours under heating. The reaction mixture was poured into 50 ml of ethyl acetate and the crystals of the dye formed were recovered by filtration and recrystallized from ethanol to provide 1.79 g of crystals of the dye. A methanol solution of the dye had a yellow-orange color and the maximum absorption wavelength thereof was 485 m$\mu$. $E_{max} = 4.5 \times 10^4$.

The colors of gelatin films dyed with the dyes prepared in Examples 23 and 24 are shown in the following table.

Also, other similar dyes having a benzothiazole nucleus or a benzoxazole nucleus and a substituent at the β-position were prepared in the same manner as described in Examples 23 and 24 and the dyes and the colors of gelatin films dyed with the dyes are also shown in the same table.

TABLE XIV

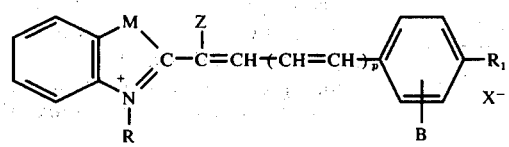

| Dye No. | Starting Material Compounds Formula II + Formula III | R | M | Z | p | X⁻ | B | R₁ | Color of Dyed Gelatin Film |
|---|---|---|---|---|---|---|---|---|---|
| I-81 | II-7 + III-57 | —C₂H₅ | S | —CH₃ | 0 | — | — | —N(CH₃)((CH₂)₃SO₃⁻) | Red |
| I-82 | II-9 + III-60 | —C₂H₅ | O | —⟨phenyl⟩ | 0 | — | — | —N(CH₃)((CH₂)₄SO₃⁻) | Yellow |
| I-83 | II-12 + III-58 | —C₂H₅ | S | —⟨phenyl⟩ | 0 | I⁻ | — | —N(CH₃)(CH₂—⟨C₆H₄⟩—SO₃K) | Red |
| I-84 | II-51 + III-59 | —C₂H₅ | O | —CH₃ | 0 | I⁻ | 2-CH₃ | —OCH₂CHCH₂SO₃Na, OH | Yellow |
| I-85 | II-54 + III-57 | —C₂H₅ | S | —CH₃ | 1 | — | — | —N(CH₃)((CH₂)₂SO₃⁻) | Purple Blue |
| I-86 | II-56 + III-60 | —C₂H₅ | O | —⟨phenyl⟩ | 1 | — | — | —O(CH₂)₃SO₃⁻ | Red |

While the invention has been described in detail and with reference to specific embodiments thereof, it will be apparent to one skilled in the art that various changes and modifications can be made therein without departing from the spirit and scope thereof.

What is claimed is:

1. A styryl and butadienyl dye having the formula (I)

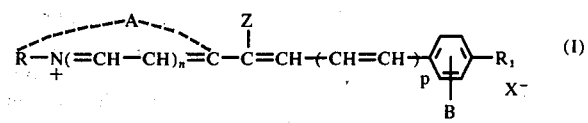

wherein R represents a lower alkyl group, a sulfo lower alkyl group, a sulfo lower alkenyl group, or a carboxy lower alkyl group; A represents the atoms necessary for forming a 5-membered or 6-membered heterocyclic ring; Z represents a hydrogen atom, a methyl group, or a phenyl group; B represents a hydrogen atom, a lower alkyl group, a hydroxyl group, an alkoxy group, a halogen atom, a nitro group, a carboxyl group, an acylamino group, an alkoxycarbonylamino group, an alkylsulfonylamino group, or an alkylthio group; R₁ represents

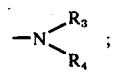

R₃ and R₄, which may be the same or different, each represents a hydrogen atom, an alkyl group, an aralkyl group, an aryl group, an arylsulfonyl group, or an acetyl group; at least one of said R₃ and R₄ containing, however, at least one sulfo group; X⁻ represents an acid anion; and n and p each represents 0 or 1.

2. The styryl and butadienyl dye as set forth in claim 1, in which Z is a hydrogen atom.

3. The styryl and butadienyl dye as set forth in claim 1, in which A is the atoms necessary for forming a thiazole nucleus, a benzothiazole nucleus, a naphthothiazole nucleus, an oxazole nucleus, a benzoxazole nucleus, a naphthoxazole nucleus, an indole nucleus, a selenazole nucleus, a benzoselenazole nucleus, a naphthoselenazole nucleus, a benzoindole nucleus, a pyridine nucleus, a quinoline nucleus, an isoquinoline nucleus or a benzimidazole nucleus.

4. The styryl and butadienyl dye as set forth in claim 1, in which Z is a hydrogen atom and said A is the atoms necessary for forming a thiazole nucleus, a benzothiazole nucleus, a naphthothiazole nucleus, an oxazole nucleus, a benzoxazole nucleus, a naphthoxazole nucleus, an indole nucleus, a benzoindole nucleus, a pyridine nucleus, a quinoline nucleus, or an isoquinoline nucleus.

5. The styryl and butadienyl dye as set forth in claim 1, in which $R_3$ and $R_4$, which may be the same or different, each represents a hydrogen atom, an alkyl group, an aralkyl group, or an aryl group.

6. The styryl and butadienyl dye as set forth in claim 1, in which B represents a hydrogen atom, a lower alkyl group, an alkoxy group, an acylamino group, an alkoxycarbonylamino group, an alkylsulfonylamino group, or an alkylthio group.

7. The styryl and butadienyl dye as set forth in claim 1, in which A represents the atoms necessary for forming an oxazole nucleus, a benzoxazole nucleus, a naphthoxazole nucleus, an indole nucleus, or a benzoindole nucleus; Z represents a hydrogen atom; B represents an alkyl group or an alkoxy group; and $R_3$ and $R_4$, which may be the same or different, each represents a hydrogen atom, an alkyl group, an aralkyl group or an aryl group.

8. The styryl and butadienyl dye as set forth in claim 1, in which the lower alkyl group for R is a methyl group, an ethyl group, a propyl group, or a butyl group; the sulfo lower alkyl group for R is a sulfoethyl group, a 3-sulfopropyl group, a 3-sulfobutyl group, a 4-sulfobutyl group, a 5-sulfopentyl group, a 1-methyl-3-sulfopropyl group, a 2-hydroxy-3-sulfopropyl group, a 2,4-diphenyl-4sulfobutyl group, a 4-ethyl-4-sulfobutyl group, or a 1,1,1,2-tetrafluoro-2-sulfoethyl group; the sulfo lower alkenyl group for R is a 3-sulfopropenyl group; the carboxy lower alkyl group for R is a 2-carboxyethyl group, a 3-carboxypropyl group or a 4-carboxybutyl group; the 5- or 6-membered heterocyclic ring formed by A is a thiazole ring, a benzthiazole ring, a naphthothiazole ring, an oxazole ring, a benzoxazole ring, a naphthoxazole ring, an indole ring, a benzindole ring, a selenazole ring, a benzselenazole ring, a naphthoselenazole ring, a pyridine ring, a quinoline ring, an isoquinoline ring, or a benzimidazole ring; the lower alkyl group for B is a methyl group or an ethyl group; the acylamino group for B is an acetylamino group, a benzoylamino group, a chloroacetylamino group, or a hydroxyacetylamino group; the alkyl group for $R_3$ and $R_4$ is an unsubstituted alkyl group or a substituted alkyl group selected from the group consisting of a cyanoalkyl group, a sulfoalkyl group, a hydroxyalkyl group, a dihydroxyalkyl group, a haloalkyl group, a carboxyalkyl group, an alkoxycarbonylalkyl group, an acylalkyl group, an acyloxyalkyl group, an alkoxyalkyl group, an aryloxyalkyl group, a cyanoalkoxyalkyl group, a dialkylaminoalkyl group, an alkylarylaminoalkyl group, an acylaminoalkyl group, an alkylsulfonylaminoalkyl group, an acylacyloxyalkyl group, an aryloxyacyloxyalkyl group, an alkylsulfonylalkyl group, an alkylsulfonyloxyalkyl group, an alkylthioalkyl group, and an alkoxycarbonyloxyalkyl group; the aralkyl group for $R_3$ and $R_4$ is an unsubstituted aralkyl group or a substituted aralkyl group selected from the group consisting of an alkoxyaralkyl group, a sulfoaralkyl group and an alkylaralkyl group and the aryl group for $R_3$ and $R_4$ is an unsubstituted aryl group or a substituted aryl group selected from the group consisting of an alkaryl group, a sulfoaryl group and an alkylsulfoaryl group.

9. A process of producing a styryl and butadienyl dye have the formula (I)

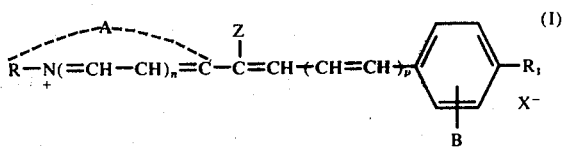

wherein R represents a lower alkyl group, a sulfo lower alkyl group, a sulfo lower alkenyl group, or a carboxy lower alkyl group; A represents the atoms necessary for forming a 5-membered or 6-membered heterocyclic ring; Z represents a hydrogen atom, a methyl group, or a phenyl group; B represents a hydrogen atom, a lower alkyl group, a hydroxyl group, an alkoxy group, a halogen atom, a nitro group, a carboxyl group, an acylamino group, an alkoxycarbonylamino group, an alkylsulfonylamino group, or an alkylthio group; $R_1$ represents

$R_3$ and $R_4$, which may be the same or different, each represents a hydrogen atom, an alkyl group, an aralkyl group, an aryl group, an arylsulfonyl group, or an acetyl group; at least one of said $R_3$ and $R_4$ containing at least one sulfo group; $X^-$ represents an acid anion; and n and p each represents 0 or 1 which comprises condensing a sulfo group-containing aldehyde compound represented by the formula (II)

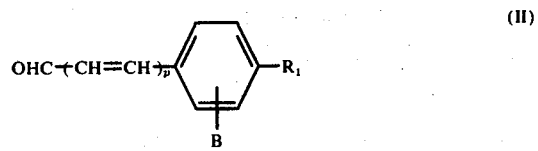

wherein B, $R_1$, and p have the same significance as in the formula (I) and a cyclic quaternary ammonium salt represented by the formula (III)

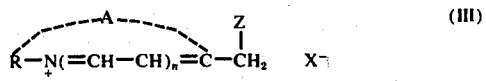

wherein A, R, Z, $X^-$, and n have the same significance as in the formula (I).

10. The process as set forth in claim 9, in which Z is a hydrogen atom.

11. The process as set forth in claim 9, in which A is the atoms necessary for forming a thiazole nucleus, a benzothiazole nucleus, a naphthothiazole nucleus, an oxazole nucleus, a benzoxazole nucleus, a naphthoxazole nucleus, a selenazole nucleus, a benzoselenazole nucleus, a naphthoselenazole nucleus, an indole nucleus, a benzoindole nucleus, a pyridine nucleus, a quinoline nucleus, an isoquinoline nucleus or a benzimidazole nucleus.

12. The process as set forth in claim 9, in which Z is a hydrogen atom and A is the atoms necessary for forming a thiazole nucleus, a benzothiazole nucleus, a naphthothiazole nucleus, an oxazole nucleus, a benzoindole nucleus, a pyridine nucleus, a quinoline nucleus, or an isoquinoline nucleus.

13. The process as set forth in claim 9, in which $R_3$ and $R_4$, which may be the same or different, each represents a hydrogen atom, an alkyl group, an aralkyl group, or an aryl group.

14. The process as set forth in claim 9, in which B represents a hydrogen atom, a lower alkyl group, an alkoxy group, an acylamino group, an alkoxycarbonylamino group, an alkylsulfonylamino group, or an alkylthio group.

15. The process as set forth in claim 9, in which A represents the atoms necessary for forming an oxazole nucleus, a benzoxazole nucleus, a naphthoxazole nucleus, an indole nucleus, or a benzoindole nucleus; Z represents a hydrogen atom; B represents an alkyl group or an alkoxy group; and $R_3$ and $R_4$, which may be the same or different, each represents a hydrogen atom, an alkyl group, an aralkyl group, or an aryl group.

16. The process as set forth in claim 8, in which the lower alkyl group for R is a methyl group, an ethyl group, a propyl group, or a butyl group; the sulfo lower alkyl group for R is a sulfoethyl group, a 3-sulfopropyl group, a 3-sulfobutyl group, a 4-sulfobutyl group, a 5-sulfopentyl group, a 1-methyl3-sulfopropyl group, a 2-hydroxy-3-sulfopropyl group, a 2,4-diphenyl-4-sulfobutyl group, a 4-ethyl-4-sulfobutyl group, or a 1,1,1,2-tetrafluoro-2-sulfoethyl group; the sulfo lower alkenyl group for R is a 3-sulfopropenyl group; the carboxy lower alkyl group for R is a 2-carboxyethyl group, a 3-carboxypropyl group or a 4-carboxybutyl group; the 5- or 6-membered heterocyclic ring formed by A is a thiazole ring, a benzthiazole ring, a naphthothiazole ring, an oxazole ring, a benzoxazole ring, a naphthoxazole ring, an indole ring, a benzindole ring, a selenazole ring, a benzselenazole ring, a naphthoselenazole ring, a pyridine ring, a quinoline ring, an isoquinoline ring, or a benzimidazole ring; the lower alkyl group for B is a methyl group or an ethyl group; the acylamino group for B is an acetylamino group, a benzoylamino group, a chloroacetylamino group, or a hydroxyacetylamino group; the alkyl group for $R_3$ and $R_4$ is an unsubstituted alkyl group or a substituted alkyl group selected from the group consisting of a cyanoalkyl group, a sulfoalkyl group, a hydroxyalkyl group, a dihydroxyalkyl group, a haloalkyl group, a carboxyalkyl group, an alkoxycarbonylalkyl group, an acylalkyl group, an acyloxyalkyl group, an alkoxyalkyl group, an aryloxyalkyl group, a cyanoalkoxyalkyl group, a dialkylaminoalkyl group, an alkylarylaminoalkyl group, an acylaminoalkyl group, an alkylsulfonylaminoalkyl group, an acylacyloxyalkyl group, an aryloxyacyloxyalkyl group, an alkylsulfonylalkyl group, an alkylsulfonyloxyalkyl group, an alkylthioalkyl group, and an alkoxycarbonyloxyalkyl group; the aralkyl group for $R_3$ and $R_4$ is an unsubstituted aralkyl group or a substituted aralkyl group selected from the group consisting of an alkoxyaralkyl group, a sulfoaralkyl group and an alkylaralkyl group and the aryl group for $R_3$ and $R_4$ is an unsubstituted aryl group or a substituted aryl group selected from the group consisting of an alkaryl group, a sulfoaryl group and an alkylsulfoaryl group.

17. The styryl and butadienyl dye as set forth in claim 1, in which A is the atoms necessary for forming an indole nucleus, Z is a hydrogen atom, and $R_3$ and $R_4$, which may be the same or different, represent alkyl groups, at least one of said $R_3$ and $R_4$ containing, however, at least one sulfo group.

* * * * *